US010258610B2

(12) United States Patent
Viscomi et al.

(10) Patent No.: US 10,258,610 B2
(45) Date of Patent: Apr. 16, 2019

(54) PHARMACEUTICAL COMPOSITIONS COMPRISING RIFAXIMIN, PROCESSES FOR THEIR PREPARATION AND THEIR USE IN THE TREATMENT OF VAGINAL INFECTIONS

(75) Inventors: Giuseppe Claudio Viscomi, Bologna (IT); Paola Maffei, Bologna (IT); Vittoria Lauro, Bologna (IT); Fiorella Calanni, Bologna (IT); Beatrice Vitali, Bologna (IT); Federica Cruciani, Bologna (IT)

(73) Assignee: ALFASIGMA S.P.A., Milan (MI) (IT)

( * ) Notice: Subject to any disclaimer, the term of this patent is extended or adjusted under 35 U.S.C. 154(b) by 0 days.

(21) Appl. No.: 13/559,013

(22) Filed: Jul. 26, 2012

(65) Prior Publication Data
US 2013/0028971 A1    Jan. 31, 2013

(30) Foreign Application Priority Data

Jul. 29, 2011 (IT) .............................. BO2011A0461

(51) Int. Cl.
A61K 31/437 (2006.01)
A61K 9/00 (2006.01)

(52) U.S. Cl.
CPC .......... *A61K 31/437* (2013.01); *A61K 9/0034* (2013.01)

(58) Field of Classification Search
CPC .... A61K 9/002; A61K 9/0012; A61K 9/0034; A61K 31/395; A61K 31/435; A61K 31/4353; A61K 31/437
USPC ......... 424/474, 465; 514/279, 385, 396, 397
See application file for complete search history.

(56) References Cited

U.S. PATENT DOCUMENTS

| 4,341,785 | A | 7/1982 | Marchi et al. |
| 5,356,625 | A | 10/1994 | Ying |
| 5,840,332 | A | 11/1998 | Lerner et al. |
| 6,140,355 | A | 10/2000 | Egidio et al. |
| 7,045,620 | B2 | 5/2006 | Viscomi et al. |
| 7,612,199 | B2 | 11/2009 | Viscomi et al. |
| 7,902,206 | B2 | 3/2011 | Viscomi et al. |
| 7,906,542 | B2 | 3/2011 | Viscomi et al. |
| 7,915,275 | B2 | 3/2011 | Viscomi et al. |
| 7,923,553 | B2 | 4/2011 | Viscomi et al. |
| 8,158,644 | B2 | 4/2012 | Viscomi et al. |
| 8,158,781 | B2 | 4/2012 | Viscomi et al. |
| 8,173,801 | B2 | 5/2012 | Viscomi et al. |
| 8,193,196 | B2 | 6/2012 | Viscomi et al. |
| 8,217,054 | B2 | 7/2012 | Maffei et al. |
| 8,318,763 | B2 | 11/2012 | Viscomi et al. |
| 8,404,704 | B2 | 3/2013 | Viscomi et al. |
| 8,518,949 | B2 | 8/2013 | Viscomi et al. |
| 8,568,782 | B2 | 10/2013 | Viscomi et al. |
| 2003/0059471 | A1 | 3/2003 | Compton |
| 2003/0157174 | A1 | 8/2003 | Tsukuda |
| 2004/0234601 | A1 | 11/2004 | Legrand |
| 2005/0196418 | A1 | 9/2005 | Yu |
| 2005/0272754 | A1 | 12/2005 | Viscomi et al. |
| 2007/0082035 | A1* | 4/2007 | Neurath et al. ............... 424/443 |
| 2008/0262024 | A1 | 10/2008 | Viscomi et al. |
| 2009/0028940 | A1 | 1/2009 | Jahagirdar et al. |
| 2009/0082558 | A1 | 3/2009 | Kothakonda et al. |
| 2009/0291854 | A1* | 11/2009 | Wiesinger-Mayr et al. ..... 506/8 |
| 2009/0312357 | A1 | 12/2009 | Rao et al. |
| 2010/0215740 | A1* | 8/2010 | Pilgaonkar et al. .......... 424/465 |
| 2010/0330129 | A1 | 12/2010 | Viscomi et al. |
| 2011/0086871 | A1 | 4/2011 | Viscomi et al. |
| 2012/0035202 | A1 | 2/2012 | Viscomi et al. |
| 2012/0077835 | A1* | 3/2012 | Selbo et al. .................. 514/279 |
| 2012/0202989 | A1 | 8/2012 | Viscomi et al. |
| 2012/0203000 | A1 | 8/2012 | Viscomi et al. |
| 2012/0214989 | A1 | 8/2012 | Viscomi et al. |
| 2013/0004576 | A1 | 1/2013 | Viscomi et al. |
| 2013/0072676 | A1 | 3/2013 | Maffei et al. |
| 2013/0281697 | A1 | 10/2013 | Viscomi et al. |
| 2013/0287692 | A1 | 10/2013 | Viscomi et al. |
| 2013/0289269 | A1 | 10/2013 | Viscomi et al. |
| 2013/0310410 | A1 | 11/2013 | Viscomi et al. |
| 2014/0235662 | A1 | 8/2014 | Viscomi et al. |

(Continued)

FOREIGN PATENT DOCUMENTS

| EP | 0161534 B1 | 9/1989 |
| EP | 0547294 A1 | 6/1993 |
| EP | 0616808 A1 | 9/1994 |

(Continued)

OTHER PUBLICATIONS

G. C. Viscomi et al., "Crystal forms of rifaximin and their effect on pharmaceutical properties", 1074-1081, 10, CrystEngComm (2008).
Descombe et al. "Pharmacokinetic study of rifaximin after oral administration in healthy volunteers" 51-56, 14(2), Int J Clin Pharmacol Res, 1994.
Debbia et al., "Effects of Rifaximin on bacterial virulence mechanism at supra and sub-inhibitory concentrations" 186-94, 20(2), J. Chemother. 2008.
Rifaximin p. 1475 Merck Index XIII ed. 2001.
"Disintegration of suppositories and pessaries" pp. 255-256, Chapter 2.9.2., European Pharmacopeia Ed. 7.0, 2008.
Donders G.G. et al., "A multicenter, double-blind, randomized, placebo-controlled study of rifaximin for the treatment of bacterial vaginosis" 131-136, 120, International Journal of Gynecology and Obstetrics. 2013.

(Continued)

*Primary Examiner* — Blessing M Fubara
(74) *Attorney, Agent, or Firm* — Steinfl + Bruno LLP

(57) ABSTRACT

The invention relates generally to pharmaceutical compositions comprising rifaximin effective at treating vaginal infections, and in particular bacterial vaginosis. The pharmaceutical compositions comprising rifaximin granules are characterized in that they release rifaximin in the vagina in a controlled way. The present invention also relates to processes for preparation of the rifaximin pharmaceutical compositions and their use in the treatment of vaginal infections. Effective dosages and courses of treatment useful and effective at recovering from the disease and preventing any possible relapse are also provided.

8 Claims, No Drawings

(56) References Cited

U.S. PATENT DOCUMENTS

2015/0073007 A1  3/2015  Viscomi et al.

FOREIGN PATENT DOCUMENTS

| | | |
|---|---|---|
| EP | 0858804 B1 | 8/1998 |
| EP | 0935417 B1 | 8/1999 |
| EP | 1557421 B1 | 7/2005 |
| EP | 1676847 B1 | 7/2006 |
| EP | 1676848 B1 | 7/2006 |
| EP | 1698630 A1 | 9/2006 |
| EP | 1698630 B1 | 9/2006 |
| EP | 1874273 B1 | 1/2008 |
| EP | 2011486 A1 | 1/2009 |
| EP | 2059232 | 5/2009 |
| EP | 2208730 A1 | 7/2010 |
| EP | 2210893 A1 | 7/2010 |
| EP | 2420226 A1 | 2/2012 |
| EP | 2421869 B1 | 2/2012 |
| EP | 2542225 B1 | 1/2013 |
| IT | 1154655 B | 1/1987 |
| WO | 2002003987 A2 | 1/2002 |
| WO | 2005044823 A2 | 5/2005 |
| WO | 2006094662 A1 | 9/2006 |
| WO | 2006094737 A2 | 9/2006 |
| WO | 2007076874 A1 | 7/2007 |
| WO | 2008029208 A1 | 3/2008 |
| WO | 2008155728 A1 | 12/2008 |
| WO | 2009008005 A1 | 1/2009 |
| WO | 2009008006 A2 | 1/2009 |
| WO | 2009108730 A2 | 9/2009 |
| WO | 2010044093 A1 | 4/2010 |
| WO | 2010122436 A1 | 10/2010 |
| WO | 2011050397 A1 | 5/2011 |
| WO | 2011061516 A2 | 5/2011 |
| WO | 2011061519 A2 | 5/2011 |
| WO | 2011088688 A1 | 7/2011 |
| WO | 2011107970 A2 | 9/2011 |
| WO | 2011110930 A2 | 9/2011 |
| WO | 2011153444 A1 | 12/2011 |
| WO | 2011156897 A2 | 12/2011 |
| WO | 2012009387 A1 | 1/2012 |
| WO | 2012009388 A1 | 1/2012 |
| WO | 2012035283 A1 | 3/2012 |
| WO | 2012038898 A1 | 3/2012 |
| WO | 2012076832 A1 | 6/2012 |
| WO | 2013017928 A1 | 2/2013 |

OTHER PUBLICATIONS

Cruciani F. et al., Efficacy of Rifaximin Vaginal Tablets in Treatment of Bacterial Vaginosis: a Molecular of Characterization of the Vaginal Microbiota 4062-4070, 56, Antimicrobial Agents and Chemotherapy. 2012.

Rifamycins p1474 Merck Index XIII ed. 2001.

Amsel R. et al., "Diagnostic Criteria and Microbial and Epidemiologic Associations" 14-22, 74(1), The American Journal of Medicine. 1983.

Nugent RP et al., "Reliability of Diagnosing Bacterial Vaginosis Is Improved by a Standardized Method of Gram Stain Interpretation" 297-301, 29(2), Journal of Clinical Microbiology. 1991.

Zhou X. et al., "Characterization of vaginal microbial communities in adult healthy women using cultivation-independent methods" 2565-2573, 150(pt8), Microbiology. 2004.

Bartosch, "Characterization of Bacterial Communities in Feces from Healthy Elderly Volunteers and Hospitalized Elderly Patients by Using Real-Time PCR and Effect" 3575-3581, 70(6), Applied and Environmental Microbiology. 2004.

CDC, Sexually Transmitted Diseases Treatment Guidelines, Dec. 17, 2010, No. RR 12, 59.

Simoes J.A. et al., "Effect of metronidazole on the growth of vaginal lactobacilli in vitro" 41-45, 9(1), Infect Dis Obstet Gynecol 2001.

Resistance to crushing of tablets p. 267, Chapter 2.9.8, European Pharmacopoeia Ed. 7.0. 2008.

PCT International Search Report dated Nov. 13, 2012 for PCT/IB2012/001438 filed on Jul. 26, 2012 in the name of Alfa Wassermann S.P.A, 7 pages.

International Preliminary Report on Patentability dated Nov. 5, 2013 for PCT/IB2012/001438 filed on Jul. 26, 2012 in name of Alfa Wassermann S.P.A, 13 pages.

Communication under Rule 71(3) EPC about the intention to grant issued by the European Patent Office dated May 7, 2015 for European Application 12761650, 5 pages.

Communication under Article 94(3) issued by the European Patent Office on Feb. 17, 2015 for the application EP12761650, 2 pages.

PCT Written Opinion dated Nov. 13, 2012 for PCT/IB2012/001438 filed on Jul. 26, 2012 in the name of Alfa Wassermann S.P.A, 4 pages.

1-Newman, A. et al., "Assessing the Performance of Amorphous Solid Dispersions" *Journal of Pharmaceutical Sciences* vol. 101, No. 4, Apr. 2012, pp. 1355-1377.

2-Harmon, P. et al., "Amorphous Solid Dispersions" Analytical Challenges and Opportunities *AAPS Newsmagazine* Sep. 2009, pp. 14-20.

3-Paudel, A. et al., "Manufacturing of solid dispersions of poorly water soluble drugs by spray drying: formulation and process considerations" *International Journal of Pharmaceutics* 453 (2013) pp. 253-284.

4-Rowe, R.C. et al., Eds. "Handbook of Pharmaceutical Excipients, Seventh Edition" Jun. 2012, pp. 227-229; pp. 757-760; pp. 784-797.

5-Rahman, B.M. et al. "Effect of starch 1500 as a binder and disintegrant in lamivudine tablets prepared by high shear wet granulation" *Pak. J. Pharm. Sci.*, vol. 21, No. 4, Oct. 2008, pp. 455-459.

\* cited by examiner

PHARMACEUTICAL COMPOSITIONS COMPRISING RIFAXIMIN, PROCESSES FOR THEIR PREPARATION AND THEIR USE IN THE TREATMENT OF VAGINAL INFECTIONS

CROSS-REFERENCE TO RELATED APPLICATIONS

This application claims the benefit of priority from Italian Application No. IT BO2011A000461 filed Jul. 29, 2011, the contents of which are incorporated herein by reference.

DESCRIPTION

Object of the Invention

The present invention relates to compositions, comprising rifaximin granules, together with pharmaceutically acceptable excipients, characterized in that the compositions have a controlled release. The present invention also describes processes for their preparation and their use in the treatment of vaginal infections, in particular of bacterial vaginosis. Furthermore, it also describes the rifaximin dosages useful and effective at recovering from the disease and preventing any possible relapse.

Background of the Invention

Rifaximin (INN, see The Merck Index, XIII ed., 8304, CAS No. 80621-81-4), IUPAC nomenclature 2S, 16Z, 18E, 20S, 21S, 22R, 23R, 24R, 25S, 26S, 27S, 28E)-5,6,21,23,25 pentahydroxy-27-methoxy-2,4,11,16,20,22,24,26-octamethyl-2,7-(epoxypentadeca (1,11,13) trienimine) benzofuro (4,5-e)pyrido(1,2,-a benzimidazole-1,15(2H)dione, 25-acetate) is a semysinthetic antibiotic drug belonging to the rifampicin group, more precisely a pyrido-imidazo-rifamycin described in IT 1154655, whereas EP 0 161 534 describes a production process starting from Rifamycin 0 (The Merck Index XIII ed., 8301).

U.S. Pat. No. 7,045,620, EP 1557421B1, EP1676847B1, EP1676848B1, WO2005/044823, WO2006/094662 describe crystalline forms α, β, γ, δ and ε of rifaximin. WO2008/155728, US 2009/312357 and US2008/008253 describe processes for obtaining amorphous forms.

WO2009/108730 describes polymorphous forms of rifaximin named zeta, eta, α-dry, iota, β-1, β-2 and ε-dry.

WO2011/153444 describes polymorphous forms κ and θ and WO 2011/156897 describes polymorphous forms named APO-1 and APO-2.

Viscomi G. et al in Cryst. Eng Comm., 2008, 10 1074-1081 (2008) describes polymorphous α, β, γ, δ, ε, the process for obtaining them and their chemical-physical and biological properties.

Rifaximin is an antibiotic drug active against Gram-positive and Gram-negative bacteria, characterized by a low systemic absorption, negligible when administered via the oral route, as described by Descombe J. J. et al. in Int. J. Clin. Pharmacol. Res., 14 (2), 51-56, (1994); it is known for its antibacterial activity, exerted, for instance, against bacteria localized in the gastrointestinal tract causing intestinal infections, diarrhea and irritable bowel syndrome (IBS), bacterial growth in the small intestine or "small intestinal bacterial overgrowth" (SIBO), is also known to be associated with Crohn's disease (CD), pancreatic insufficiency, enteritis, fibromyalgia.

For this characteristic, rifaximin plays a relevant role in the therapy of infectious and inflammatory bowel diseases, both in the acute and in the chronic phase.

The different forms of rifaximin are associated to different levels of systemic absorption. Rifaximin is presently authorized for the treatment of acute and chronic pathologies whose etiology is partially or completely referable to Gram-positive and Gram-negative intestinal bacteria, such as diarrheic syndromes caused by an altered balance of the intestinal microbial flora such as summer diarrheas, traveler's diarrhea and enterocolitis. Rifaximin is useful in the pre- and post-surgical prophylaxis of infectious complications in the gastroenteric tract surgery, as an adjuvant in hyperammonaemias therapy and in the reduction of the risk of acute episodes of hepatic encephalopathy.

Rifaximin can also be useful in treating the "restless-legs syndrome"; for the prevention of spontaneous bacterial peritonitis in patients affected by hepatic insufficiency and in the infections induced by the chronic use of proton pump inhibitors.

Furthermore, the fact that rifaximin is poorly absorbed systemically is advantageous for the aforesaid applications, since rifaximin is not toxic, even at high doses and reduces the incidence of undesired side effects such as, for instance, the selection of antibiotic-resistant bacterial strains and the risk of possible pharmacological interactions.

Rifaximin characteristics make it a compound useful in topical treatments, such as those useful for treating vaginal infections, for example bacterial vaginosis.

Bacterial vaginosis is an extremely frequent pathology, representing 40-50% of all vaginal infections. When it is symptomatic and without complications, bacterial vaginosis is characterized by malodorous vaginal discharges not associated to an inflammatory clinical picture (vaginosis), and is attributed to an alteration of the vaginal ecosystem.

The normal vaginal flora of a healthy woman, because to the prevailing presence of *Lactobacilli*, in particular *Lactobacillus crispatus* and *gasseri*, produces hydrogen peroxide and maintains an acid vaginal pH, thus inhibiting the growth of most pathogenic microorganisms.

In bacterial vaginosis, *Lactobacillus* bacteria is replaced by an excessive growth, even a thousand times higher than normal values, of facultative anaerobic and aerobic bacteria, mainly represented by *Gardnerella vaginalis*, which is present in nearly all women affected by bacterial vaginosis, by *Mycoplasma hominis*, by Gram-negative anaerobic bacteria such as *Bacteroides* and *Prevotella*, by anaerobes such as *Peptostreptococcus*, by Gram-positive anaerobes such as *Mobiluncus*, which is present in 50% of the cases, and by Gram-positive bacilli such as *Atopobium vaginale*, which is present in 95% of cases of bacterial vaginosis.

Factors predisposing the onset of the disease are mainly formed in fertile-aged women having a low socioeconomic level, belonging to the black race, regularly using vaginal lavages, smoking and having sexual intercourse with several different partners. On the other hand, taking estroprogestinic drugs seems to play a protective role. Also the hormonal component turned out to be involved in its aetiopathogenesis, since this pathology is mainly found in fertile-aged women.

Bacterial vaginosis can be related to several serious gynecological and obstetrical complications, such as, for instance: pelvic inflammatory disease, frequent cause of sterility and ectopic pregnancy; infection of surgical injury after gynecologic surgery; premature rupture of the membranes in pregnant women; premature labor and abortion.

Furthermore, although it is not considered a sexually transmitted disease, bacterial vaginosis is associated to an increased risk of catching sexually transmitted pandemic diseases, including the HIV virus infection, both for non-pregnant and pregnant women. In these latter, it also determines an increase of the risk of transmission of HIV virus from the mother to the fetus.

The diagnosis of bacterial vaginosis can be based upon clinical and/or microbiological criteria.

The clinical diagnosis is carried out according to Amsel clinical criteria, as described by Amsel R. et al. in Am. J. Med. 1983; 74(1): 14-22. The diagnosis is positive when at least three out of the four following symptoms are reported: 1) vaginal discharges which are homogeneous and adhering to the vaginal walls; 2) whiff test positivity (development of "fishy odor" after the addition of 10% potassium hydroxide to vaginal discharge); 3) vaginal pH higher than 4.5, and 4) an amount greater than 20% of clue cells (squamous epithelium vaginal cells coated with bacteria, identified by fresh microscopic examination).

The microbiological diagnosis is based on the calculation of the Nugent score, which includes microscopic examination of vaginal discharges by means of Gram staining. The presence and the quantity of three different vaginal bacterial species is determined. In particular, a low score is obtained if the *Lactobacilli* concentration is high, the score increases if the presence of *Gardnerella* and *Bacteroidi* is ascertained, and the score is even higher if also the presence of *Mobiluncus* is ascertained. A resulting score between 0 and 3 is representative of vaginal flora of a healthy woman, a score between 4 and 6 indicates that vaginal flora is starting to be altered, and a score between 7 and 10 indicates a certain diagnosis of bacterial vaginosis, as described by Nugent R P et al. in J. Clin. Microbiol. 1991, 29(2), 297-301.

Moreover, in recent years further diagnostic molecular techniques have been developed, such as PCR-DGGE and real-time PCR, based upon the sequence analysis of RNA and allowing the identification of a microbial composition of the vaginal ecosystem, as described by Zhou X et al. in Microbiology 2004, 150 (Pt8), 2565-2573 and in Appl. Environ. Microbiol. 2004, 70(6), 3575-3581. Therefore, these techniques can be directly used to determine the presence of pathogenic agents causing the disease and also to verify the effect of therapy on them from the quantitative point of view.

Although the bacterial vaginosis etiology is not completely understood, the treatment has the aim of inducing both a clinical and a microbiological recovery and when possible avoiding the relapse infections. Therefore, an ideal therapy should be effective at reducing pathogenic species and at the same time, it should also encourage the restoration and proliferation of *Lactobacillus* protective species with the aim of preventing possible disease relapses.

The guidelines of the Center of Disease Control (CDC), 2010, 59, NoRR-12 state that all women affected by bacterial vaginosis, which are symptomatic and non-pregnant, should be treated with antibiotic therapy.

In this regard, CDC suggests, as first therapeutic approach, antibiotic treatments such as, for instance: metronidazole, oral tablets 500 mg, twice a day for 7 days; or metronidazole, vaginal gel, 0.75%, an applicator (5 g once a day for 5 days or clindamycin, vaginal cream, 2%, an applicator (5 g) once a day for 7 days.

Both metronidazole and clindamycin, administered either via the systemic route (orally) or via local route (vaginally), are effective at treating bacterial vaginosis. However, the inhibitory action of both active principles against *Lactobacillus* protective flora, as described by Simoes J A et al in Infect. Dis. Obstet. Gynecol. 2001, 9(1), 41-45, limits its efficacy at preventing relapses.

Furthermore, both of the above mentioned antibiotics are associated with systemic side effects, some of them particularly relevant, such as, for instance, neurological reactions for metronidazole or pseudomembranose colitis for clindamycin, even when administered via vaginal route.

Moreover, if repeatedly administered, both metronidazole and clindamycin can induce microbiological resistances not only at the vaginal level, but also at the systemic level, since they are systemically absorbed even after vaginal administration.

EP 0547294 describes compositions containing rifaximin amounts between 50 and 500 mg which are stated to be useful in treating vaginal infections caused by microorganisms susceptible to rifaximin. In particular, EP 0547294 describes a clinical trial carried out with a preparation of rifaximin vaginal foam and cream, containing 200 mg rifaximin, stating the higher efficacy of foam if compared to the cream. This document also describes compositions for treating bacterial vaginosis containing rifaximin in capsules, ovules and tablets and it also describes the antibacterial action of rifaximin against bacteria commonly present in the vaginal discharge is described. Table 1 of EP 0547294 describes that rifaximin exerts an important antibacterial activity both against pathogenic bacteria such as *Gardnerella vaginalis, Bacteroides bivious-disiens, Mobiluncus* and also against non-pathogenic bacteria such as *Lactobacilli*.

The inhibition of *Lactobacilli*, whose presence is beneficial for maintaining the healthy vaginal environment, must be considered a detrimental event with regard to therapeutic efficacy. In fact, as already stated, the acid environment generated by *lactobacilli* is an essential condition for preventing pathogenic bacteria colonization.

Table 1 of EP 0547292 also shows that rifaximin inhibitory action ($MIC_{50}$ and $MIC_{90}$) against *Lactobacilli* is equal to, or even higher than, its action against pathogenic bacteria, such as, for instance, *Gardnerella vaginalis, Mobiluncus* spp, *Bacteroides bivius-disiens*. Thus, when administered via the vaginal route, rifaximin indiscriminately acts on the whole bacterial flora, including *Lactobacilli*.

Debbia A. et al. describes in J. Chemother. 20, (2), 186-194, 2008 that rifaximin exhibits a time-dependent bacterial activity, therefore, new rifaximin pharmaceutical compositions are needed that are effective in treating vaginal infections, providing for an appropriate period of time of exposure to rifaximin and local concentrations of rifaximin useful in treating vaginal infections, such as for bacterial vaginosis, and that do not reduce the *Lactobacilli* concentration, which is important for the prevention of relapse of vaginal infections. Moreover, it was important that the rifaximin concentrations provided by the composition are effective without requiring high doses of rifaximin.

Taking into account the intense color of rifaximin, it was also important that the rifaximin containing compositions were well accepted by patients without causing colored discharging, and that the compositions were preferably in a solid dosage form.

It was also important that the pharmaceutical compositions would be effective at eradicating the disease (vaginal infections) and at reducing the number of relapses with shorter periods of treatment and with reduced total amounts of administered rifaximin when compared to that described in EP 0547294.

An object of the present invention, which is now surprisingly accomplished, are solid pharmaceutical compositions, in particular in the form of vaginal tablets, specifically tablets formed by compressing rifaximin granules with extra granular excipients. The rifaximin granules are characterized in that the rifaximin granules contain pharmaceutically acceptable excipients chosen among diluent, binder and lubricant, wherein at least a binder is present. The extragranular excipients are characterized in that the extragranular excipients comprise at least one disintegrant and optionally other extragranular excipients chosen from binder, diluent and lubricant.

The pharmaceutical compositions of the present invention are characterized in that they release rifaximin comprised in granules in a short time, even in environment with reduced amounts of water such as those physiologically present in the vagina. The compositions sufficiently disintegrate the granules in the vagina and provide rifaximin in effective amounts for treating vaginal infections.

The new compositions can be prepared with different rifaximin polymorphs already known in the art, and are useful in treating bacterial vaginosis and in preventing relapses of the disease.

In particular, the new compositions do not diminish the Lactobacilli concentration naturally present in vaginal flora, but unexpectedly favor their increase during the course of treatment.

The compositions, object of the present invention, provide useful in the treatment of vaginal infections, and in particular of bacterial vaginosis, at doses less than 200 mg/day, with a course of treatment of less a week and provide recovery with lower rifaximin amounts over a course of treatment shorter than those reported in the literature available to the expert of the art and in the clinical praxis, thus obtaining a recovery from the disease with totally administered rifaximin amounts which are about ten times lower that those mentioned in the patent EP 0547294. In particular the invention provides effective doses and course of treatment useful in obtaining a complete recovery, in particular in comparison to the placebo.

The pharmaceutical compositions comprising rifaximin, object of the present invention, are effective at treating vaginal infections, and in particular bacterial vaginosis, at concentrations lower than 200 mg/day, with a duration of treatment shorter than a week, if compared to the placebo.

Beside doses, the present invention also selects a duration of treatment useful in obtaining a complete recovery.

The found compositions turned out to be accepted, well tolerated and devoid of side effects.

SUMMARY OF THE INVENTION

Exemplary embodiments described herein overcome the above described drawbacks of conventional rifaximin compositions by providing pharmaceutical compositions comprising rifaximin, effective at treating vaginal infections, and in particular bacterial vaginosis.

One aspect of the invention are pharmaceutical compositions comprising rifaximin granules having rifaximin in an amount less than 500 mg, e.g., less than 200 mg, preferably between 2.5 and 100 mg, e.g., 12.5, 25 mg, 50 mg and 100 mg, and one or more of an extragranular excipient including at least one disintegrant; wherein said pharmaceutical composition has selective bactericidal activity against vaginal pathogenic bacteria. Another aspect of the invention is a pharmaceutical composition characterized as having selective antibacterial action that maintains or increases the amount of Lactobacilli after a course of treatment.

The pharmaceutical composition may have at least one extragranular disintegrant present in an amount preferably between 2-20% by weight of the pharmaceutical composition.

The pharmaceutical composition may be a controlled release formulation and may be in the form of a vaginal tablet or ovule. Preferably, the pharmaceutical composition is in the form of a vaginal tablet. The vaginal tablet may have a disintegration time of less than five minutes, preferably of less than two minutes.

Also presently described are new methods of i) treating a vaginal infection (e.g., bacterial vaginosis) and ii) preventing relapse of a vaginal infection (e.g., bacterial vaginosis), the methods comprising vaginally administering a therapeutically effective amount of the described pharmaceutical composition wherein the therapeutically effective amount selectively reduces an amount of vaginal pathogenic bacteria while maintaining or increasing an amount of Lactobacilli over a course of treatment. In one aspect of the presently disclosed method, the amount of Lactobacilli increases over the course of treatment.

In one embodiment, the therapeutically effective amount may be a rifaximin daily dose of less than 500 mg, preferably 200 mg, e.g., less than 100 mg. Preferably, the rifaximin daily dose is 100 mg, 50 mg or 25 mg.

The course of treatment is preferably ten days or less, e.g., one week or less. The amount of rifaximin administered over the course of treatment may be 700 mg rifaximin or less, e.g., 500 mg rifaximin or less.

The therapeutically effective amount of rifaximin may be 12.5 or 25 mg per day wherein the course of treatment is 5 days. Alternatively, in another embodiment, the therapeutically effective amount of rifaximin per day may be 100 mg and wherein the course of treatment is 2 days.

In one embodiment, the method of treating a vaginal infection according to the present invention causes a reduction in the Nugent score by 3 points or more after the course of treatment.

Also presently described is a process of making the pharmaceutical composition comprising the steps of forming rifaximin granules by dry granulating a mixture of the rifaximin and one or more intragranular excipients, forming a tablet by first mixing and then compressing the rifaximin granules with the one or more of an extragranular excipient including at least one disintegrant. In a preferred embodiment, by using the disclosed process, the form of rifaximin before the dry granulating step and the form of rifaximin after the dry granulating step are the same form.

DESCRIPTION OF THE INVENTION

The present invention describes pharmaceutical compositions comprising less than 200 mg of rifaximin in a solid form, in particular in a form of tablets, characterized in that they release rifaximin in a controlled manner, providing a selective bactericidal activity against pathogenic bacteria.

The pharmaceutical compositions of the present invention are characterized in that, they comprise rifaximin granules and/or microgranules with extragranular excipients. The rifaximin granules comprise excipients chosen among one or more of diluent, binder and lubricant agents; the extragranular excipients comprise one or more of binder, diluent, lubricant and disintegrant agents.

The pharmaceutical compositions in solid form, in particular in the form of tablets, provide fast disintegration, e.g., less than five minutes, and enable the release of rifaximin granules even in the presence of low amounts of aqueous liquid, such as the vaginal mucosa.

In one embodiment the pharmaceutical composition comprises rifaximin granules and/or microgranules comprising less than 200 mg rifaximin, preferably less than 100 mg rifaximin. The new composition further comprises one or more intragranular excipients, and one or more extraganular excipients including at least one disintegrant. The intragranular excipients are selected from the group consisting of a diluent, binder, lubricant and mixtures thereof. The extragranular excipients include at least one disintegrant and optionally additional extragranular excipients selected from the group consisting of binders, diluents, lubricants and mixtures thereof.

The granules comprising rifaximin, are characterized in that they comprise a rifaximin amount between 1 and 80% (w/w), one or more binders in an amount between 0.5 and 20% (w/w), one or more diluents in an amount between 30 and 90% (w/w), one or more lubricants in an amount between 0.1 and 5% with respect to the granule weight.

According to a preferred embodiment of the invention, the rifaximin granules comprise a rifaximin amount between 5 and 30% (w/w), one or more binders in an amount between 1 and 10% (w/w), one or more diluents in an amount between 50 and 90% (w/w) and one or more lubricants in an amount between 0.5 and 4% (w/w), with respect to the weight of the granule.

The diluent suitable for the preparation of rifaximin granules is preferably chosen from the group comprising cellulose, microcrystalline cellulose, hydroxypropyl methylcellulose, calcium phosphate, starch, kaolin, di-hydrated calcium sulphate, calcium carbonate, anhydrous or hydrated lactose, saccharose, mannitol, polysaccharides, glucans, xyloglucan and mixture thereof.

The binder suitable for the preparation of rifaximin granules is chosen in the group comprising corn starch, pregelatinized starch, arabic gum, lactose, maltodextrine, copolymer of 1 vinyl-2 pyrrolidone and vinylacetate (copovidone), saccharose and mixtures thereof.

The lubricant suitable for the preparation of rifaximin granules is chosen in the group comprising glycerol dibehenate, calcium or magnesium stearates, aluminum, sodium stearyl fumarate, hydrogenated oils, vegetable oils, palmitic acid, alcohol, starch, mineral oils, polyethylene glycol, sodium lauryl sulphate, talc, glycerides, sodium benzoate and mixture thereof.

According to a preferred embodiment of the present invention, the binder is chosen in the group consisting of copovidone and corn starch. More preferably, the binder is copovidone.

According to a preferred embodiment of the present invention, the diluent is chosen in the group consisting of monohydrate or anhydrous lactose, cellulose and macrocrystalline cellulose, hydroxypropyl methylcellulose. More preferably, the diluent is monohydrate or anhydrous lactose.

According to a preferred embodiment of the present invention, the lubricant is chosen in the group consisting of magnesium stearate and glycerol dibehenate. More preferably, the lubricant is magnesium stearate.

The rifaximin granules are prepared by means of the dry granulation process wherein rifaximin is mixed with the chosen excipients (intragranular excipients), in the above mentioned amounts, and the whole is then mixed to obtain a homogeneous mixture. The mixture is then placed in a compactor for obtaining granules.

The rifaximin granules are then further processed and mixed with extragranular excipients, including at least one of the disclosed disintegrant.

The additional extragranular excipients are selected from the group consisting of a binder, diluent and lubricant agent and combination thereof.

According to a preferred embodiment, the binder is chosen in the group comprising copovidone, pregelatinized starch and corn starch; the diluent is chosen in the group consisting of lactose, cellulose, microcrystalline cellulose and hydroxypropyl methylcellulose; the lubricant is chosen in the group consisting of magnesium stearate and glycerol dibehenate.

The disintegrant agent suitable for the preparation of the composition according to the present invention is chosen in the group consisting of: sodium starch glycolate, pregelatinized starch, polyvinyl pyrrolidone copolymer (PPPV or crospovidone), sodiumcarboxy methyl cellulose (carmellose sodium), crosslinked carboxy methyl cellulose (crosscarmellose sodium), silicates of alkaline and alkaline earth metals (e.g. calcium silicate) and mixture thereof.

Preferably, the extragranular disintegrant is chosen from the group consisting of: crospovidone, sodium starch glycolate, pregelatinized starch, silicates of alkali metals and mixture thereof.

More preferably, the extragranular disintegrant is chosen in the group consisting of: crospovidone, calcium silicate and mixture thereof. In particular and in a proffered embodiment the disintegrant is a mixture of crospovidone and calcium silicate.

According to a preferred embodiment of the present invention the solid pharmaceutical composition, preferably in the form of tablets, can contain rifaximin granules in an amount between 10 and 85% (w/w), disintegrant(s) or their mixture, wherein the total amount is between 2 and 20% (w/w), independently from their relative ratios, binder in an amount between 0.5 and 5.0% (w/w), lubricant in an amount between 0.1 and 10.0% (w/w), with respect to final composition as reported in Table 1.

TABLE 1

| Component | Percentage (%) by weight |
| --- | --- |
| Rifaximin granules | 10-85% |
| Lubricant | 0.1-10% |
| Binder | 0.5-5% |
| Diluent | 10-80% |
| Disintegrant | 2-20% |

According to a preferred embodiment of the present invention, the extragranular diluent is chosen in the group consisting of: anhydrous or monohydrate lactose, corn starch and crystalline cellulose; the extragranular lubricant is magnesium stearate, the binder is chosen among pregelatinized starch and copovidone, hydroxy propyl methyl cellulose, and the extragranular disintegrant is chosen among crospovidone, pregelatinized starch and calcium silicate and mixture thereof.

According to a more preferred embodiment, the extragranular diluent is chosen in the group comprising anhydrous or monohydrate lactose; the extragranular binder is chosen in the group comprising copovidone and pregelatinized starch; the extragranular lubricant is magnesium stearate; the extragranular disintegrant is chosen in the group comprising crospovidone, calcium silicate, pregelatinized starch and starch glycolate.

According to a more preferred embodiment, the tablet composition, comprising rifaximin is reported in Table 2.

TABLE 2

| Component | Percentage (%) by weight |
| --- | --- |
| Rifaximin granules | 20-60% |
| Magnesium stearate | 0.1-10% |
| Copovidone | 0.5-4% |
| Lactose | 10-80% |
| Crospovidone and calcium silicate | 2-20% |

The tablet composition may further comprise a coating such as a filmogen coating.

The solid composition in the form of tablets can contain a rifaximin amount between 2.5-500 mg, preferably between 2.5-100 mg, more preferably between 10-50 mg.

The solid composition in the form of tablets can also contain rifaximin in an amount preferably between 10 and 100 mg, between 10 and 50 mg and between 10 and 25 mg, more preferably between 25 and 100 and between 25 and 50 mg and most preferably 25 mg.

The composition according to the present invention can optionally further contain bioadhesive agents, preservative agents, buffering agents, antiseptic agents and fragrances.

When the biohadesive agent is present, the composition can have bioadhesive properties, which means that the rifaximin granules can adhere to the vaginal mucosa.

Examples of polymers and oligomers or their mixtures which can be included in microgranules are pectins, zeins, casein, gelatin, albumin, collagen, kitosan, oligosaccharides and polysaccharides such as, for example, cellulose, dextran, polysaccharides from tamarind seeds, xanthan gum, Arabic gum, hyaluronic acid, alginic acid, sodium alginate.

When the bioadhesive is a synthetic polymer, the polymer is chosen among polyamides, polycarbonates, polyalkylenes, polyalkylene glycols, polyalkylene oxides, polyalkylene terephthalates, polyvinyl alcohol, polyvinyl ethers, polyvinyl esters, polyvinyl pyrrolidone, polysiloxanes, polyurethanes, polystyrenes, polymers of acrylic acid and methacrylate esters, copolymer of methacrylic acid-ethyl acrylate, polyactides, polybarbituric acids, polyanhydrides, polyorthoesters and mixtures thereof. Other useful polymers are methyl cellulose, ethyl cellulose, hydroxy propyl cellulose, hydroxy butyl methylcellulose, cellulose acetate, cellulose propionate, cellulose acetate butyrate, carboxy methyl cellulose, cellulose triacetate, cellulose sulfate sodium salt, polymethyl methacrylate, poly-isopropyl methacrylate, poly-isobutyl acrylate, poly(octadecyl acrylate), polypropylene, polyethylene glycol, polyethylene oxide, polyethylene terephthalate, polyvinyl acetate, polyvinyl chloride, polystyrene, polyvinyl pyrrolidone, polyvinyl phenol and mixtures thereof.

Another group of polymers useful for obtaining the bioadhesiveness are polymers having a branching group comprising at least one bound hydrophobic group, wherein the hydrophobic groups are generally non polar groups. Non-limiting examples of such hydrophobic groups include alkyl, alkenyl and alkynyl groups. Preferably, the hydrophobic groups are chosen to increase the bioadhesiveness of polymers. Other polymers are characterized by hydrophobic branching with at least a hydrophilic group, such as carboxy acids, sulphonic acids and phosphonic acids, neutral and positively charged amines, amides and imines, wherein the hydrophilic groups are such that they increase the bioadhesiveness of the polymer.

The rifaximin granules are obtained by means of a dry granulation process, which allows to maintain the starting rifaximin crystalline or amorphous form without any polymorphic transformations that occur as described in literature, in the presence of water or organic solvents.

A preferred process for obtaining the composition retains the selected polymorphic form, since it is known in the art that forms of rifaximin polymorphs have different solubility and give plasma absorptions differing by at least two orders of magnitude.

The term "rifaximin" is intended in the broad sense and includes not only "rifaximin" but also its pharmaceutically acceptable salts, solvates, hydrates, derived enantiomers, polymorphs, amorphous forms, co-crystals and pharmaceutically acceptable complexes, with no limitations.

Rifaximin comprised in the pharmaceutical compositions object of the present invention is preferred in a poorly soluble form when it is used for treating bacterial vaginosis in order to act locally without systemic absorption. This avoids at the systemic level a potential selection risk of antibiotic-resistant bacterial strains which can occur, even at low plasma concentrations.

By selecting different polymorphs of rifaximin, characterized for having different dissolution and absorption, or a mixture thereof, it is possible to prepare composition, and in particular in the form of tablets, for the treatment of vaginal infections, and more in particular for different states of infection.

The rifaximin granules are then mixed with the mixture comprising the extragranular excipients as described in Table 1; the mixture is compressed in a compression machine, known in the art for obtaining tablets which are preferably coated with a filmogen coating.

The extragranular components present in the pharmaceutical composition in the form of tablets, together with rifaximin granules, in the amounts described in the present invention, allow the controlled release of rifaximin.

The rifaximin granules are released from the tablets even in the environment with reduced amounts of aqueous liquid, such as the physiological environment present in the vagina. The rifaximin granules released by the tablets in the vaginal cavity exert a topical action in the vaginal mucosa for a proper period of time due to the combined effect of the fast tablet disintegration rate and reduced rate of granules dissolution.

The present invention also describes the use of rifaximin pharmaceutical compositions for treating vaginal infections, for example particular bacterial vaginosis.

The present invention also provides a method of treating bacterial infection and a method of preventing relapse of bacterial infection by administering the new composition. In particular the pharmaceutical compositions object of the present invention, when administered with the disclosed method of treatment do not reduce the *Lactobacilli* concentration, which are necessary for maintaining the vaginal ecosystem and useful in preventing relapsing infections like those reported with respect to the compositions known in the art.

The solid pharmaceutical compositions, of the present invention are therapeutically effective at treating bacterial infections at rifaximin daily doses lower than 500 mg, preferably less than 200 mg, more preferably less than 100 mg and with a total rifaximin administered less than 700 mg, more preferably less than 500 mg, for obtaining the complete recovery and the relapse prevention in comparison to the placebo.

In particular, the compositions in form of tablet comprising rifaximin are effective at treating bacterial infections as evidence by the reduction of the Nugent score and Amsel criteria, by administering therapeutically effective daily doses less than 500 mg, preferably less than 200 mg and more preferably less than 100 mg, e.g. 100 mg, 50 mg, 25 mg 12.5 or 2.5 mg, for a treatment time shorter than ten days and in particular shorter than one week, in comparison to the placebo.

The tablet compositions can be administered once or several times a day, preferably once a day.

The described pharmaceutical compositions are characterized in that they exert a selective antibacterial action, preferably against pathogenic bacteria, rather than against *Lactobacilli*.

The composition in form of tablets comprising rifaximin, in amounts less than 500 mg, in particular less than 200 mg and more in particular less than 100 mg, increase and keep the *Lactobacilli* concentration high even after the end of the course of the treatment when compared to the placebo.

Another aspect of the present invention is providing a composition and course of therapy useful in treating vaginal infections, in both obtaining recovery and preventing relapse of patients suffering from bacterial infections.

In particular, the described compositions maintain the recovery from the disease for a time period longer than 30 days at the end of a therapy comprising daily administration doses less than 200 mg, preferably less than 100 mg for an administration time less than one week.

Another particular aspect of the new pharmaceutical compositions, comprising an amount of rifaximin between 12.5 mg and 100 mg, is to be useful in treating vaginal infections with treatment times shorter than one week. More in particular, the compositions containing 25 mg rifaximin with a five-day treatment time are shown to be in particular useful in treating bacterial infections.

Patients treated with the compositions comprising 25 mg rifaximin who received a tablet once a day for five days show a higher recovery rate (percent of patients exhibiting recovery at the end of course therapy), according to Nugent score and Amsel criteria, higher than the one showed by placebo-treated patients.

In particular, patients treated with the compositions comprising 25 mg rifaximin for five days show a higher recovery rate of, i.e., 48%, compared to about 25.9% recovery rate of patients treated with 100 mg rifaximin for five days, about 36% recovery rate of patients treated with 100 mg/day for two days and about 19.2% recovery rate of placebo-treated patients, as reported in Table 18.

More in particular, patients treated with the compositions comprising 25 mg rifaximin, show a higher recovery rate, according to Nugent score, higher than the one obtained by other treated groups. In particular, a higher recovery rate of 47% if compared to about 25% recovery rate of patients treated with 100 mg rifaximin for five days, about 36% recovery rate of patients treated for two days and about 19% recovery rate of placebo-treated patients.

Another aspect of the present invention is given by the fact that the compositions comprising rifaximin in vaginal tablets lead to a three-point reduction of the Nugent score in all treated patients if compared to the placebo-treated patients.

In particular, a three-point reduction of the Nugent score is obtained by a percentage higher than about 65% in the group of patients treated with the vaginal tablet composition comprising 25 mg rifaximin for five days; by a percentage higher than 50% of the patients treated with the composition comprising 100 mg rifaximin for five days; by a percentage higher than 30% of patients in the group treated with the tablet composition comprising 100 mg rifaximin for two days, if compared to a percentage of about 18% of placebo-treated patients.

Moreover, and in particular, vaginal tablet compositions comprising 25 mg rifaximin, when administered to patients affected by bacterial vaginosis for a course of treatment of five days led to a five-point reduction of the Nugent score in about 48% of treated patients, about 28% of patients treated with rifaximin 100 mg for five days and about 26% of patients treated with 10 mg for two days, when compared to a percentage of about 0% of placebo-treated patients.

Furthermore, and more in particular, the vaginal tablet compositions comprising 25 mg rifaximin for a course of treatment time of five days lead to a 8-10 point reduction of the Nugent score in a higher percentage when compared to the other treatment groups, including in this study.

The described pharmaceutical compositions, due to the property of the combination of selected granular and extragranular excipients and the preparation process, provide a controlled release of rifaximin in the vagina such as to be effective with only one dosage administration a day.

The described pharmaceutical compositions are useful and effective at treating patients affected by vaginal infections, in particular bacterial vaginosis, at daily doses lower than 200 mg, and in particular at doses comprised between 100 and 25 mg, e.g. 100 mg, 50 mg 25 mg and 12.5 mg rifaximin, rifaximin with treatment times shorter than one week.

Another aspect of the described compositions comprising 25 mg rifaximin in form of vaginal tablets is that they are useful in treating patients affected by vaginal infections, in particular severe bacterial vaginosis, characterized in that they have a high Nugent score ($\geq 6$, preferably $\geq 7$, or more preferably, $\geq 9$ or according to 3 out of 4 factors among the Amsel criteria).

Another aspect of the present invention is the use of the rifaximin compositions, comprising rifaximin at concentrations less than 200 mg, and in particular of 100 mg, 50 mg 25 mg and 12.5 mg, according to the disclosed treatment time to treat cure and prevent a relapse of bacterial vaginosis.

Another aspect of the present invention is represented by pharmaceutical compositions comprising rifaximin characterized in that they are well tolerated and safe when administered, and in particular in that they result in a reduced systemic absorption showed by the negligible level of rifaximin measured in plasma.

The solid pharmaceutical compositions in the form of tablets, have the unexpected property to release rifaximin granules in vaginal mucosa even with reduced amounts of vaginal liquid. The results of a clinical trial of the present invention show that said granules are able to release rifaximin amounts effective in patients affected by bacterial vaginosis even with treatments with low doses of rifaximin and course of treatment, e.g. not longer than ten days and, in particular, not longer than five days, and are able to prevent relapse infections through four weeks after the end of a course of treatment.

Moreover, it is particularly essential that the tablet composition comprising rifaximin amounts lower than 200 mg, and in particular lower than 100 mg, increases and keeps high the *Lactobacilli* concentration even after the end of the therapy if compared to the placebo.

Example 1 describes the preparation of rifaximin granules and the preparation of vaginal tablets comprising 25 mg rifaximin. The tablets are prepared by mixing the rifaximin granules together with extragranular excipients.

The obtained tablets have a hardness, determined as described in European Pharmacopeia Ed. 7.0, Chapter 2.9.8, ref, 01/2008:20908, higher than 5 Kp and are characterized in that they have a disintegration time, under the conditions described in European Pharmacopeia Ed. 7.0, Chapter 2.9.2. ref. 01/2008:20902, of about one minute.

Example 2 describes the preparation of 100 mg rifaximin tablets, wherein the rifaximin granules are mixed together with extragranular excipients, showing the flexibility of the tablet production process, also when variable amounts of rifaximin without increasing the weight of the finished tablet. Example 3 describes the preparation of rifaximin tablets wherein the granules are prepared with different binders, in respect to those used in Example 1, and they are mixed with extragranular excipients.

In particular, Example 3 describes the preparation of compositions wherein different excipients are used in comparison with Example 1 and 2.

In particular, the disintegrant is chosen from calcium silicate, crospovidone, sodium starch glycolate, or their mixture; the binder is the hydroxypropyl methylcellulose and the diluent is monohydrate lactose.

This composition 7, wherein binder is not present in the extragranular excipients illustrate a problem in the formation of the mixture and by visual inspection the mixture did not appear as homogeneous in the absence of binder. Example 4 reports the disintegration time obtained according to European Pharmacopeia European Pharmacopoeia 7.0 2.9.2, ref. 01/2008:20902, of the of rifaximin tablets in Compositions 1-8, prepared according Examples 1, 2 and 3. The disintegration time varies between about one minute and ten minutes depending on the components comprised in the compositions; the composition without any disintegrant (Comp. 4), gives a disintegration time of about 5 minutes and when only crospovidone is present (Comp. 3, 5 and 6), the disintegration time is between 1'30" and 5'30". The lower disintegration time of composition 3 corresponds to a composition wherein a higher amount of crospovidone is added.

The lower disintegration times exhibited by the composition 1, composition 2 and composition 7, are preferred, but the composition 7 is not presently preferred for industrial scale.

Composition 1 and 2 correspond to the tablets comprising rifaximin in an amount of 25 and 100 mg characterized in that the intragranular binder is copovidone and the extragranular disintegrant is a mixture of crospovidone and calcium silicate. These compositions are able to disintegrate in a time less than 2 minutes and release rifaximin at the site of action.

Example 5 describes the preparations of lipophilic ovules wherein rifaximin is between 50 and 200 mg in the presence of semi glycerides, surfactants and xyloglucan. The rifaximin amount released by the lipophilic ovules after about two hours is from between 15% and 25% in respect to the total rifaximin comprised in the ovules.

Example 6 describes the preparation of hydrophilic ovules wherein rifaximin is comprised between 25 and 100 mg in the presence of 2(2-ethoxyethoxy)ethanol, Transcutol, glycerin, polyethylene glycol (PEG) and xyloglucan. These compositions are characterized by a fast release of rifaximin and the released rifaximin is higher than 70% (w/w) after 20 minutes.

Example 7 describes the release of compositions in tablets and vaginal ovules prepared as in Examples 1-5, in a solution with a volume and temperature conditions similar to vaginal physiologic conditions. The different compositions comprising from 25 to 100 mg rifaximin are compared to evaluate the rifaximin release in a thermostated environment at 37° C. The amount of rifaximin released in 10 ml aqueous solution is determined spectrophotometrically. The described experiments show that the tablets comprising 100 mg rifaximin, prepared as described in Example 1 and having the composition described in Example 2, release after one hour, an amount of rifaximin smaller than about 0.5 mg; the hydrophilic ovules comprising 100 mg rifaximin release after one hour about 8.5 mg rifaximin, the hydrophilic ovules comprising 25 mg rifaximin release after one hour about 7 mg rifaximin and the lipophilic ovules comprising about 100 mg rifaximin release after one hour about 4 mg rifaximin.

Example 8 describes a bioavailability study has been carried out with the pharmaceutical compositions in tablets described in the present invention, wherein tablets and ovules containing an amount of rifaximin corresponding to 12.5 mg prepared by means of a process identical to the one described in Examples 1 and 4 have been administered to female New Zealand White Specific Pathogen free (SPF) rabbits, nulliparous and non-pregnant. During the treatment, no local clinical signs were observed, neither reactions to the treatment, nor body weight variations of the treated animals if compared to the control group.

The rifaximin concentration in plasma was determined by a validated LC-MS/MS method having a Lower Limit of Quantitation (LLOQ) of 0.5 ng/ml.

Table 15 of Example 8 reports the pharmacokinetic parameters of rifaximin in rabbit after the administration of vaginal tablets and ovules. Only in some cases the pharmacokinetic parameters are slightly above the LLOQ. The average value of the maximum plasma concentration ($C_{max}$) for the ovules is about four times higher than the $C_{max}$ value of the tablets, whereas the value of the area subtended by the plasma concentration curve related to the time (AUCO-t last) of the ovules is about twelve times higher if compared to the one of the tablets.

These results show that, by administering the same dosage of rifaximin, the vaginal tablets give a lower plasma absorption if compared to the ovules. This result is in accord with the dissolution profiles showed in Example 7.

Example 9 describes the efficacy of rifaximin compositions in ovules and tablets in an animal model, wherein the vaginal infection was induced by means of inoculation of *Gardnerella vaginalis* isolated in women affected by bacterial vaginosis. New Zealand rabbit having a weight comprised between 2 and 3 kg were infected with a saline solution containing an amount of *Gardnerella vaginalis* larger than 105 and, in order to obtain a persistent infection, the inoculation was repeated twice or thrice. Seven days after the last inoculation the animals were treated with the rifaximin compositions in tablets and ovules containing rifaximin amounts comprised between 1.5 and 12.5 mg, whose preparation was carried out according to Example 1 and Example 4, wherein the excipients ratio was proportionally reduced in order to obtain compositions with different amounts of rifaximin. The rifaximin doses comprised between 1.5 mg and 12.5 mg respectively correspond to a dose of about 12.5 mg and 100 mg in women, calculated according to the body surface area.

The compositions did not show any adverse event in the animals and showed, as reported in Tables 16 and 17. The tested rifaximin dosages both in tablets and in ovules lead to a complete eradication of the infection seven days after the end of the treatment.

Both ovules and tablets compositions turned out to be effective and well tolerated by the animals. However, since tablets have lower systemic absorption levels than the ovules, as described in Example 8, must be considered a more suitable pharmaceutical preparation to be used for patients affected by bacterial vaginosis.

The clinical study described in Example 12 was carried out with tablets comprising 25 and 100 mg rifaximin, prepared as described in Examples 1 and Example 2.

Examples 10 and 11 describe the systemic absorption and the tolerability of rifaximin tablets in a clinical study on healthy volunteers. The example shows that the plasma concentrations of rifaximin after administration via the intravaginal route of a tablet containing 100 mg rifaximin are neglectable because they are always below the instrumental LLOQ of 0.5 ng/ml.

The efficacy of the composition in tablets at treating bacterial vaginosis was determined by means of a clinical study carried out on 114 non-pregnant women having an age comprised between 18 and 50 years, and reported in Example 12. The clinical study described in Example 12 was carried out with tablets comprising 25 and 100 mg of rifaximin as prepared as described in Example 1 and 2.

The primary end point of this trial was the evaluation of the recovery from bacterial vaginosis according to Nugent score and Amsel criteria at the first control visit (V3) 7-10 days after the end of the therapy.

The secondary end point of this trial was the recovery from the disease singularly evaluated according to Nugent score and Amsel criteria, 7-10 days after the end of the therapy, the maintenance of recovery at the second control visit about one month after the end of the therapy (V4) and the evaluation of the composition of vaginal microbiota by means of molecular techniques, real-time PCR— and PCR-DGGE (Polymerase Chain Reaction-Denaturing Gradient Gel Electrophoresis). The real-time PCR— is a quantitative technique wherein each DNA sample is amplified with different gender- and/or species-specific primers whose target is the 16S rRNA bacterial gene or the 16S-23S rRNA region; in particular, specific probes were used for the *Lactobacillus* gender, for *Gardnerella vaginalis*, for *Atopobium*, for *Prevotella* and for *Veillonella*, since they represent the main bacterial groups suffering from modifications in case of bacterial vaginosis. On the other hand, PCR-DGGE is a qualitative technique, so that in the present study, the amplification was carried out with universal primers of eubacteria.

In particular, patients affected by bacterial vaginosis and not affected by contemporaneous viral, protozoan and fungal vaginal infections, were assigned to one of the following treatment groups, using a centralized randomization procedure and a double-blind experimental design:

Group A: patients receiving a vaginal tablet of rifaximin containing 100 mg rifaximin, prepared according to Example 2, once a day for five days, in the evening;

Group B: patients receiving a vaginal tablet of rifaximin containing 25 mg rifaximin, prepared according to Example 1, once a day for five days, in the evening;

Group C: patients receiving a vaginal tablet of rifaximin containing 100 mg rifaximin, prepared according to Example 2, once a day for two days, in the evening, plus a vaginal tablet of placebo, once a day for the remaining three days, in the evening;

Group D: patients receiving a placebo tablet prepared according to Example 1, wherein the rifaximin amount was replaced by hydrated lactose, once a day for five days, in the evening.

The diagnosis of bacterial vaginosis was based on Amsel criteria (at least three out of four positive criteria) and on Nugent score (equal to or higher than 4). The study included a screening visit (V1) followed by a randomization visit after seven days (V2), by a first control visit 7-10 days after the end of the therapy (V3) and by a second and last control visit 28-35 days after the end of the therapy (V4). The evaluation of the attainment of the primary end point was carried out during visit V3, and the evaluation of the attainment of the secondary end point was evaluated during visit V4.

Table 18 reports the percent values of patients after treatment with the composition prepared according to Example 1 and Example 2 in comparison to those treated with placebo. It is point out from the clinical trial that all groups of patients treated with the rifaximin tablet compositions showed a percent recovery greater than those treated with placebo.

Patients belonging to the group treated with a tablet containing 25 mg rifaximin prepared according to Example 1 for five days showed a percent recovery from the disease greater than the one of the other groups.

More in particular, patients belonging to the group treated with a tablet containing 25 mg rifaximin (Group B) prepared according to Example 1 for five days, showed a percent recovery greater than 40%; those treated with a rifaximin tablet containing 100 mg rifaximin for two days (Group C) showed a percent recovery greater than 30%; those treated with a tablet containing 100 mg rifaximin for five days (Group A) showed a percent recovery greater than 20%. The placebo-treated group (Group D) showed a percent recovery of just about 19%.

Table 19 reports percent values of patients, calculated according to Amsel criteria 7-10 days after the end of the therapy. This result confirms that the group who received the composition containing 25 mg rifaximin for five days showed a percent recovery greater than the placebo-treated group.

Table 20 reports that according to Nugent score, at visit V3, the percent recovery from the disease is greater in patients belonging to the group treated with the composition comprising 25 mg rifaximin for five days, Group B is greater than to the other groups and to the placebo treated group.

In this example describing the clinical study, patients were further classified in "patient with bacterial vaginosis relapse" and "patient with first occurrence of bacterial vaginosis". The percent recovery from the disease in all rifaximin-treated groups was greater in patients suffering from a bacterial vaginosis relapse. Moreover, the group treated with 25 mg rifaximin for five days showed a higher percent recovery even in subjects suffering from the first occurrence of the disease.

The percent recovery from the disease, evaluated according to Nugent score and Amsel criteria, in all groups treated with rifaximin turned out to be higher in patients suffering from a bacterial vaginosis infection if compared to patients suffering from a first occurrence of bacterial vaginosis. Furthermore, the group treated with rifaximin 25 mg for five days, Group B, showed a higher percent recovery also in subjects suffering from the first occurrence of the disease, as reported in Table 23.

Patients treated with 25 mg and 100 mg rifaximin in vaginal tablets in the clinical study did not show any particular adverse event and none of the treated groups showed any case of rifaximin-related vulvovaginal candidiasis during treatment.

The reported clinical study showed that the treatment of patients affected by bacterial vaginosis with controlled release vaginal tablets prepared according to Example 1 and containing 25 mg rifaximin once a day, for five days is more effective at recovering from the disease.

Examples 13-16 describe the obtainment of recovery, according to Nugent criteria, in the four groups of patients enrolled in the clinical study Group A, B, C and D. Example 17 reports a microbiological study carried out on vaginal rinses of patients treated with 100 mg and 25 mg rifaximin for five days (Groups A and B) and 100 mg rifaximin for two days (Group C) using molecular techniques, real-time PCR— and PCR-DGGE for determining the composition of vaginal microbiota.

Table 28 of Example 17 reports the results obtained by real-time PCR expressed as "ng target DNA/μg total genomic DNA", for microbial species, analyzed according to the group of patients involved in the clinical study, visits V3 and V4, if compared to the data obtained by means of the analysis before the treatment.

The results of real-time PCR analysis show a *Lactobacilli* increase in all groups treated with rifaximin, whereas the concentrations of pathogenic bacteria such as *Gardnerella vaginalis, Atopopium* and *Prevotella* showed a reduction in all groups treated with rifaximin, if compared to placebo, thus showing the efficacy of the composition in tablets.

In particular, patients treated with rifaximin in tablets prepared according to Example 1 and comprising 25 mg rifaximin for five days at visit V3 show a *Lactobacilli* increase if compared to the other treated groups.

Furthermore, the treatment with controlled release tablets, comprising 25 mg rifaximin for a five-day treatment turned out to be the most effective, both for its activity against anaerobic bacteria and for restoring *Lactobacilli*, thus favoring the physiological vaginal microenvironment.

The analysis of vaginal samples at visit V4 confirmed the data obtained at the visit V3 at the end of the treatment for patients treated with the composition in vaginal tablets containing 25 mg rifaximin prepared according to Example 1 for a five-day treatment, since the *Lactobacilli* concentration was maintained, whereas the pathogenic bacteria were further reduced. This result confirm the selective bactericidal action of the composition described in Example 1 and 2 between pathogenic vaginal bacteria and not against *Lactobacilli*.

Also the group of patients treated with the composition in tablets comprising 100 mg, Group A rifaximin for five days at the visit V4 maintained the rate observed at the third visit 7-10 days after the end of the therapy. The results obtained by means of the real-time PCR method were confirmed by the PCR-DGGE data, and reported in Example 18, showing the efficacy of rifaximin treatment at modulating the composition of vaginal microbiota. Also with this technique the rifaximin dosage which is most effective at modulating vaginal microbiota is the one obtained with the treatment by means of tablets containing 25 mg rifaximin, once a day for five days.

Example 18 describes the surprising and unexpected result given by the compositions in tablets containing rifaximin described in the present invention and the results of the concentrations of vaginal microbiota at visit V4 are reported in Table 29. The described composition in vaginal tablets comprising rifaximin at treatment doses of 100 mg/5 days, 25 mg/5 days and 100 mg/2 days are effective at maintaining low concentrations of pathogenic bacteria and increasing the *Lactobacilli* concentration if compared to placebo.

In particular, treatment group A, which received a tablet comprising 100 mg rifaximin for five days shows a twentyfold increase of *Lactobacilli* concentration; treatment group B, which received a tablet comprising 25 mg rifaximin for five days shows a fortyfold increase of *Lactobacilli* concentration, and treatment group C, which received a tablet comprising 100 mg rifaximin for two days shows an eightfold increase of *Lactobacilli* concentration.

The results reported in Table 29 show the selective action that rifaximin composition in tablets forms, prepared as Examples 1 and 2, favor the *Lactobacilli* colonization. The *Lactobacilli* amount at the visit V4 of Groups B and C, and in particular in Group B is the prevalent if compared to the pathogenic species present in patients treated with rifaximin, whereas it remains a minority *Lactobacilli* amount in patients treated with placebo, also in those who showed a recovery.

This evidence supports the hypothesis that patients treated with rifaximin preparations can maintain the recovery, whereas the others will probably suffer from a relapse.

The described composition in vaginal tablets is useful in recovering from the vaginal infection, and in particular the composition comprising 25 mg rifaximin administered for five days maintains a low concentration of pathogenic bacteria for about one month after the end of the treatment, and leads to an increase of *Lactobacilli* concentration in the vagina.

Example 19 describes the definition of DGGE profiles of women treated with rifaximin showing a smaller number of bands indicating the presence of a smaller number of pathogenic species if compared to the starting profiles.

Table 30 reports the percentage of women having "clusterizing" profiles, wherein it is confirmed a higher intra-variability in women treated with rifaximin if in comparison to the ones treated with placebo. In particular, it is observed that the treatment with tablets comprising 25 mg rifaximin for five days has a stronger impact on vaginal microbiota, leading to percent value smaller than the one of the other treated groups.

In order to evaluate the pharmacological action of the examined rifaximin composition, different treatment groups were compared by means of the so called "Similarity Indexes (SI)".

Table 31 reports the SI (Similarity Index) average values confirming that the rifaximin treatment restores a less complex and more physiological vaginal microenvironment.

Another criterion used for evaluating the samples is the so called "Richness Index (R1)". This criterion, based on the bands of each DGGE profile, gives the measure of the complexity of the bacterial population, which is a sign of disease for the insurgence of new pathogenic species. Table 32 reports the R1 average values measured at visits V1 and V3.

The results of Table 32 show that vaginal microbiota profiles become less complex in groups treated with rifaximin preparations if compared to the placebo-treated group.

The present invention discloses pharmaceutical compositions in controlled release tablets, comprising rifaximin, useful in treating bacterial vaginosis with negligible systemic absorption, which are able to release rifaximin, also in presence of small amount of aqueous solutions. In particular, the described compositions act selectively versus photogenic bacteria maintaining and favoring the *Lactobacilli* increase of the vaginal flora.

Moreover, the compositions of the present invention, are effective in reducing photogenic bacteria, favoring the *Lactobacilli* of the vaginal flora, after only a single daily dosage.

Kit are also provided herein, for example kit comprising the vaginal tablets, comprising effective comprising the vaginal tablets, comprising effective amount of rifaximin for treating patients with vaginal infections and instruction for using said compositions.

Same examples relate to vaginal tablets comprising different amounts of rifaximin and excipients, processes for their production, the in vivo study in animals and on affected women by vaginal infections are reported.

Example 1

Preparation of Rifaximin Comprising Vaginal Tablets: Composition 1

Solid compositions comprising 25 mg rifaximin have been prepared by means of a process comprising the following steps:

a) preparing granules comprising rifaximin and mixing the granules in a matrix comprising a mixture of disintegrants; b) compacting the granules and obtaining the tablets; c) coating of the obtained tablets with film coating.

An amount of rifaximin corresponding to 375 g is mixed with the excipients for preparing the granulate, in the respective quantities as reported in Table 3.

The excipients, copovidone, hydrated lactose hydroxy propyl methyl cellulose and hydrated lactose were previously sieved through 1.0 mm mesh sieve. Magnesium stearate, previously sieved through 0.5 mesh sieve, was then added to the mixture, in the amounts reported in Table 3.

TABLE 3

| Components | Granule components amounts (g) | Percentage (%) by weight |
|---|---|---|
| Rifaximin | 375 g | 11.1 |
| Copovidone (Kollidon VA 64) | 84.4 g | 2.5 |
| Hydrated lactose (Tablettose 80) | 2881.8 g | 85.4 |
| Magnesium Stearate | 33.8 g | 1.0 |
| Total weight | 3375 g | |

The components are placed in a mixer and mixed for 20 minutes at 15 rpm.

The mixture was then placed in a rotating compactor by applying a pressure of 75 bar for obtaining the granules.

The obtained granulate was mixed with calcium silicate (Rxcipient FM1000), crospovidone (Kollidon CL), hydrated lactose (Tablettose 80) and copovidone (Kollidon VA64) in the amounts reported in Table 4, previously sieved through 1 mm mesh sieve by using an 80 I BIN-like apparatus (Bin) for 20 minutes at 15 rpm. Magnesium stearate was then added, previously sieved through 0.5 mesh sieve and the final mixture was stirred for three minutes at 10 rpm.

The final composition of vaginal tablets is reported in Table 4.

TABLE 4

| Components | Components amounts (g) | Percentage (%) by weight |
|---|---|---|
| Rifaximin granulate | 3375 g granulate 1 | 18.75% (2.1% rifaximin) |
| Calcium Silicate (Rxcipient FM1000) | 2250 g | 12.5% |
| Crospovidone (Kollidon CL) | 540 g | 3.0% |
| Lactose-monohydrate (Tablettose 80) | 11390.5 g | 63.3% |
| Copovidone (Kollidon VA64) | 253.2 g | 1.4% |
| Magnesium stearate | 191.2 g | 1.1% |
| Total weight | 18000 g | |

The mixture obtained in step a) was compressed in a compressing machine for obtaining 22.8×10.15 mm sized tablets.

The tablets were coated by a film coating. The tablets, preheated at 45° C., are placed in a steel vessel wherein a filmogen solution was sprayed, said solution being formed by 0.22 kg Opadry II Pink dispersed in 2.88 kg water. Opadry II Pink was a powder mixture formed by titanium dioxide, red iron oxide, yellow iron oxide, polyvinyl alcohol and polyethylene glycol.

The filmogen dispersion was sprayed on the tablets until a tablet average weight corresponding to 1248 mg+5% (1185.6-1310.4 mg) was obtained.

The spraying step there was contemporaneous with a drying step of the tablets. After reaching the desired weight, the spraying step was stopped and the drying step was continued, controlling the tablet water content until a water content lower than or equal to 5% was obtained.

The tablets were then kept in moisture-preserving vessels, such as sheets made of three white, aluminum-coated, PVC/PE/PVDC layers whereon a PVDC layer is spread. The final composition (Composition 1) of the obtained tablets is reported in Table 5.

TABLE 5

| Component | Composition 1 | Percentage (%) by weight |
|---|---|---|
| Rifaximin | 25 mg | 2.0 |
| Magnesium stearate | 15 mg | 1.2 |
| Copovidone (Kollidon VA 64) | 22.5 mg | 1.8 |
| Crospovidone (Kollidon CL) | 36 mg | 2.9 |
| Calcium silicate or (RxCipient FM 1000) | 150 mg | 12.0 |
| Lactose-monohydrate (Tablettose 80) | 951.5 mg | 76.2 |
| Filmogen coating (Opadry II pink 85F34503) | 48 mg | 3.8 |
| Total weight | 1248 mg | |

The obtained tablets have average weight between 1185.6 and 1310.4 mg and hardness of about 14.75 Kp.

Example 2

Preparation of Vaginal Tablets Comprising 100 mg Rifaximin

The tablets were prepared as described in Example 1, and Table 6 reports the final composition of tablets comprising 100 mg rifaximin.

The tablets were obtained starting from a granulate having the same composition of the granulate reported in Example 1, Table 3, to which the excipients were mixed before the subsequent compression in order to obtain the final composition reported in Table 6.

TABLE 6

| Component | Composition 2 | Percentage (%) by weight |
|---|---|---|
| Rifaximin | 100 mg | 8.0 |
| Magnesium stearate | 15 mg | 1.2 |
| Copovidone (Kollidon VA 64) | 22.5 mg | 1.8 |
| Crospovidone (Kollidon CL) | 36 mg | 2.9 |
| Calcium silicate (RxCipient FM 1000) | 150 mg | 12.0 |
| Lactose monohydrate (Tablettose 80) | 876.5 mg | 70.2 |
| Filmogen coating (Opadry II pink 85F34503) | 48 mg | 3.8 |
| Total weight | 1248 mg | |

Example 3

Preparations of Vaginal Tablets Comprising 25 mg Rifaximin (Compositions 3-8)

Compositions 3-8, comprising 25 mg rifaximin, were prepared according to a process as described in Example 1.

The composition of granules comprising rifaximin, binder, diluent and lubricant is reported in Table 7.

TABLE 7

| Component | Granule A (mg) | Granule B (mg) | Granule C (mg) |
|---|---|---|---|
| Rifaximin | 25.00 | 25.00 | 25.00 |
| Magnesium stearate | 2.25 | 2.25 | 2.25 |

TABLE 7-continued

| Component | Granule A (mg) | Granule B (mg) | Granule C (mg) |
|---|---|---|---|
| Copovidone (Kollidon VA 64) | 5.63 | — | — |
| Hydroxypropyl methylcellulose (Pharmacoat 606) | — | — | 4.5 |
| Lactose monohydrate (Tablettose 80) | 192.12 | 197.75 | 197.75 |

Rifaximin comprising granules having the compositions described in Table 7, Compositions A, B, C are mixed with the extragranular excipients as described in Example 1.

Compositions 3-8 are reported in Table 8.

TABLE 8

| Component | Comp. 3 (mg) | Comp. 4 (mg) | Comp. 5 (mg) | Comp. 6 (mg) | Comp. 7 (mg) | Comp. 8 (mg) |
|---|---|---|---|---|---|---|
| Granulate | Granulate A (225 mg) | Granulate A (225 mg) | Granulate A (225 mg) | Granulate A (225 mg) | Granulate B (225 mg) | Granulate C (225 mg) |
| Magnesium Stearate | 12.75 | 12.75 | 12.75 | 12.75 | 12.75 | 12.75 |
| Copovidone (Kollidon VA) | 16.88 | 16.88 | 16.88 | 16.88 | — | — |
| Crospovidone (Kollidon CL) | 60.00 | — | 36.00 | 36.00 | 36.00 | 36.00 |
| Calcium silicate | — | — | — | — | 150.00 | 150.00 |
| Sodium starch glycolate | — | 96.00 | 24.00 | — | — | — |
| Pregelatinized starch | — | — | — | 150.00 | — | — |
| Hydroxypropyl methylcellulos | — | — | — | — | — | 16.88 |
| Lactose-monohydrate | 885.37 | 849.37 | 885.37 | 759.37 | 776.25 | 759.37 |
| Filmogen coating | 30.8-43.5 | 30.8-43.5 | 30.8-43.5 | 30.8-43.5 | 30.8-43.5 | 30.8-43.5 |

Comp. = Composition

Composition 7 showed, by visual inspection, a consistent dishomogeneity of the powder with the presence of large aggregates.

Example 4

Determination of Disintegration Time of Rifaximin Tablets; Compositions 1-8

Disintegration times of tablets with the compositions 1-8, prepared according to Examples 1, 2 and 3 were obtained as described in European Pharmacopoeia 7.0 2.9.2, ref. 01/2008:20902.

Tablets having Compositions 1-8 are placed on a net in a water bath heated at 37° C. and the lower part of the tablet is on contact with water.

The tablet disintegration times are evaluated both visually and, if necessary, by means of a glass rod for verifying its loss of consistence. The analysis was repeated on six tablets and the average time was calculated.

The obtained results are reported in Table 9.

TABLE 9

| | Comp. 1 | Comp. 2 | Comp. 3 | Comp. 4 | Comp. 5 | Comp. 6 | Comp. 7 | Comp. 8 |
|---|---|---|---|---|---|---|---|---|
| Disintegration time | 1'40" | 1'35" | 1'50" | 5'00" | 2'30" | 5'30" | 1'45" | 5'30" |

Example 5

Preparation of Lipophilic Ovules Comprising Rifaximin and Evaluation of Rifaximin Release Ovules containing 50 mg and 200 mg rifaximin, in the presence of semi-glycerides with surfactant (Suppocire BS2X) in the presence and in the absence of xyloglucan, have been prepared. The respective compositions have the amounts reported in Table 10.

The ovules have been prepared by melting semi-glycerides at 40° C. and successively dispersing the other components in the melted mass of the triglyceride. The melted mass was then placed in the special moulds and cooled for obtaining the ovules.

TABLE 10

| Component | OV-LIP. 1 (mg) | OV-LIP. 2 (mg) | OV-LIP. 3 (mg) | OV-LIP. 4 (mg) | OV-LIP. 5 (mg) |
|---|---|---|---|---|---|
| Rifaximin | 200 | 200 | 50 | 50 | 100 |
| Xyloglucan | — | 30 | — | 30 | — |
| Suppocire BS2X (semi-glycerides) | 2800 | 2770 | 2950 | 2720 | 2900 |

An ovule of each OV-LIP composition 1-5, reported in Table 10, was then placed in a cylinder containing 900 ml water at 37° C. under stirring and the amount of rifaximin released in time is determined by spectrophotometry and reported in Table 11.

The experiments were repeated in six different vessels and the average obtained value was determined.

TABLE 11

| Time (min.) | Dissolution values (μg/ml) | | | | |
|---|---|---|---|---|---|
| | OV-LIP. 1 | OV-LIP. 2 | OV-LIP. 3 | OV-LIP. 4 | OV-LIP. 5 |
| 0 | 0.0 | 0.0 | 0.0 | 0.0 | 0.00 |
| 5 | 0.8 | 0.6 | 0.8 | 1.8 | n.d |
| 10 | 1.6 | 2.1 | 1.2 | 1.4 | 0.20 |
| 20 | 3.4 | 1.9 | 2.8 | 2.0 | n.d |
| 30 | 4.1 | 3.0 | 3.6 | 3.3 | 0.28 |
| 40 | 4.3 | 3.4 | 3.7 | 2.7 | 0.35 |
| 50 | 4.8 | 3.8 | 4.3 | 2.8 | n.d |
| 60 | 5.8 | 4.8 | 4.8 | 3.7 | 0.37 |
| 70 | 7.2 | 5.0 | 5.9 | 5.2 | n.d |
| 80 | 8.4 | 6.9 | 6.5 | 6.5 | n.d |
| 90 | 9.4 | 7.9 | 7.0 | 7.2 | n.d |
| 100 | 10.2 | 11.8 | 7.7 | 8.0 | n.d |
| 110 | 18.6 | 13.6 | 9.5 | 10.0 | n.d |
| 120 | 21.1 | 16.5 | 16.4 | 19.0 | n.d |

Example 6

Preparation of Hydrophilic Ovules Comprising Rifaximin and Evaluation of Rifaximin Release Ovules containing 100 mg rifaximin with excipients and with different amounts of these latter in order to evaluate their effect on rifaximin release, have been prepared.

The six compositions of hydrophilic ovules (OV-IDR 1-6) and the relative compositions are reported in Table 12.

TABLE 12

| Component | Composition (mg) | | | | | |
|---|---|---|---|---|---|---|
| | OV-IDR. 1 | OV-IDR. 2 | OV-IDR. 3 | OV-IDR. 4 | OV-IDR. 5 | OV-IDR. 6 |
| Rifaximin | 100 | 100 | 100 | 100 | 100 | 25 |
| Transcutol | 400 | 400 | 250 | — | — | 400 |
| Glycerin | 400 | 400 | 250 | 400 | 800 | 400 |
| Xyloglucan | 150 | — | 150 | 150 | 150 | 150 |
| PEG 4000 | 1950 | 2100 | 1950 | 1950 | 1950 | 2025 |
| Water | — | — | 300 | 400 | — | — |

A hydrophilic ovule with OV-IDR compositions 1-6 was placed in a cylinder containing 90 ml water and the rifaximin amount was determined by spectrophotometric analysis. The test was repeated on six ovules.

The rifaximin amounts relating to compositions 5-9, released in time, are reported in Table 13.

TABLE 13

| Time (min.) | Dissolution values (μg/ml) | | | | | |
|---|---|---|---|---|---|---|
| | OV-IDR. 1 | OV-IDR. 2 | OV-IDR. 3 | OV-IDR. 4 | OV-IDR. 5 | OV-IDR. 6 |
| 0 | 0.00 | 0.00 | 0.00 | 0.00 | 0.00 | 0.00 |
| 5 | 22.30 | 29.41 | 3.16 | 1.35 | 25.72 | n.d. |
| 10 | 37.85 | 57.99 | 6.33 | 2.64 | 49.15 | n.d. |
| 20 | 56.92 | 105.81 | 12.07 | 3.38 | 91.60 | 0.38 |
| 30 | 66.39 | 124.15 | 15.23 | 3.62 | 112.72 | 0.64 |
| 40 | 72.30 | 127.45 | 16.63 | 3.72 | 115.00 | n.d. |
| 50 | 76.26 | 102.55 | 17.16 | 3.72 | 101.45 | 0.60 |
| 60 | 78.81 | 59.28 | 17.27 | 3.76 | 78.08 | 0.70 |
| 70 | 79.29 | 35.07 | 17.32 | 3.77 | 53.12 | n.d. |
| 80 | 77.23 | 24.69 | 17.29 | 3.76 | 35.28 | n.d. |
| 90 | 72.52 | 19.70 | 15.93 | 3.77 | 16.12 | n.d. |
| 100 | 65.62 | 16.98 | 15.86 | 3.77 | 12.42 | n.d. |
| 110 | 60.35 | 15.31 | 20.74 | 3.77 | 10.35 | n.d. |
| 120 | 54.76 | 14.09 | 23.73 | 4.87 | 0.00 | n.d. |

Example 7

Comparison of the Release of Rifaximin from Vaginal Tablets, Hydrophilic and Lipophilic Ovules A lipophilic ovule containing 100 mg rifaximin, prepared according to Example 5, and a hydrophilic ovule prepared according to Example 6, respectively containing 25 and 100 mg rifaximin and a tablet prepared according to Example 2 containing 100 mg rifaximin were placed in a bag containing 10 ml water in an environment heated at 37° C. The rifaximin amount released was measured at regular time intervals. The experiment was repeated thrice for each composition.

The rifaximin released by the examined compositions was measured in time by means of UV spectrophotometry and the rifaximin concentrations are reported in Table 14.

TABLE 14

| Time (min.) | Dissolution values (mg/ml) | | | |
|---|---|---|---|---|
| | OV-IDR. 1 | OV-IDR. 6 | OV-LIP. 5 | Tablets Composition 2 |
| 0 | 0.00 | 0.00 | 0.00 | 0.00 |
| 15 | 0.56 | 0.38 | 0.21 | 0.06 |
| 30 | 0.56 | 0.64 | 0.28 | 0.07 |
| 45 | 0.63 | 0.61 | 0.40 | 0.11 |
| 60 | 0.82 | 0.70 | 0.37 | 0.05 |

OV-IDR. 1: prepared as in Example 6 and containing 100 mg rifaximin;
OV-IDR. 6: prepared as in Example 6 and containing 25 mg rifaximin;
OV-LIP. 5: prepared as in Example 2 and containing 100 mg rifaximin.

Example 8

Bioavailability Study in Rabbit by Intravaginal Route of Rifaximin when Administered in Vaginal Tablets and Ovules Twelve female New Zealand White Specific Pathogen free (SPF) rabbits, nulliparous and non-pregnant (6 in each group) were treated with vaginal tablets and ovules containing 12.5 rifaximin prepared as in Example 1 and 4, in single dose. During the treatment no local clinical signs, no treatment reaction, no variation of body weight were observed in the treated animals if compared to the control group.

The heparinized blood was taken from the marginal ear vein, predose and about 1, 2, 4, 6, and 24 hours after the administration. The rifaximin concentration in plasma was determined by a validated LC-MS/MS method with a LLOQ of 0.5 ng/ml.

The pharmacokinetic analysis was carried out according to a standard non-compartmental analysis and the following pharmacokinetic parameters were calculated:

$C_{max}$: maximum concentration determined in plasma $t_{max}$: time necessary to reach the max plasma concentration $AUC_{(0-t\ last)}$: area subtended by the plasma concentration curve related to the time from t=0 (predose) to last time (last quantifiable concentration)

$AUC_{(inf)}$: area subtended by the plasma concentration curve related to the time from t=0 to t=infinity Table 15 reports pharmacokinetic parameters after administration of vaginal tablets and ovules containing 12.5 mg rifaximin.

TABLE 15

| | Pharmacokinetic parameters | | | |
|---|---|---|---|---|
| Preparations | $t_{max}$ (hour) | $C_{max}$ (ng/ml) | $AUC_{(0-tlast)}$ (ng/ml) | $AUC_{(inf)}$ (ng/ml · h) |
| Ovules | 2 | 6.06 ± 5.38 | 26.74 ± 28.31 | 20.57 (n = 2) |
| Tablets | 1 | 1.48 ± 0.8 | 2.12 ± 1.08 | N/C |

Example 9

Determination of Efficacy of Rifaximin Compositions in Ovules and Vaginal Tablets, in an Animal Infection Model The efficacy of vaginal compositions in rifaximin containing tablets and ovules was evaluated in an animal model of bacterial infection persistent in the rabbit.

The vaginal infection model was induced by inoculation of *Gardnerella vaginalis* isolated from women affected by bacterial vaginosis. The bacterial strains were grown in agar of bovine red blood cells at 37° C. by adding a DIFCO-C supplement and were kept under controlled atmosphere 5% CO2 for 24-48 hours.

For developing the model of animal infection, New Zealand rabbits (*Oryctolagus cunicolis*) having a weight comprised between 2 and 3 kg were used.

The animals were anesthetized by injecting via intramuscular route a mixture of ketamine (30 mg/kg) and xylazine (2 mg/kg) both at the time of inoculation and at the time of administration of rifaximin in tablets or ovules.

Before the infection, the animals had been treated with 1 ml 10% enrofloxacin solution for reducing the endogenous *Lactobacilli* and facilitating the growth of pathogenic agent. The infection was induced by inoculating in the animals vagina 1 ml of sterile saline solution containing 106-7 UFC (Unit Forming Colony) of *Gardnerella vaginalis* by using a 22-24G Teflon catheter. The presence of *G. vaginalis* in the animals was verified before the inoculation and 24 and 48 hours after the inoculation.

The animals were inoculated twice and thrice at time intervals of three days. After 14 days the last inoculation all animals were treated with 1 ml 10% enrofloxacin solution to verify the model sensitivity to antibiotics. The treatment healed the infection, thus confirming that the model can be used to evaluate the efficacy of antibiotics administered via the intravaginal route.

The presence of *G. vaginalis* was verified by vaginal buffer 1, 2, 4, 10 and 14 days after the last inoculation, putting the vaginal buffers in agar plates of bovine red blood cells with DIFCO-C supplement and growing them at 37° C. for 48 hours. The presence of *G. vaginalis* was verified by means of microscope (1000×) morphological identification and with Gram staining.

The animals with persistent infection were then treated with tablets and ovules containing rifaximin in the amounts 1.5, 3, 6 and 12.5 mg.

The compositions in form of tablets containing rifaximin for the animal studies, were prepared according to Example 1, wherein the excipients ratio is proportionally reduced in order to obtain compositions with different rifaximin amounts.

The ovules for the animal studies, were prepared according to Example 5, composition OV-2, wherein the excipients were proportionally reduced in order to obtain compositions with different rifaximin amounts.

A rifaximin containing vaginal ovule or tablet was inserted in the vagina and, in the case of vaginal tablets, 1 ml physiological solution at 37° C. was introduced to facilitate the tablet disintegration. No adverse event was observed during treatment.

Three and seven days after the end of the rifaximin treatment, the presence of *Gardnerella vaginalis* was evaluated by means of vaginal buffers as previously described.

The vaginal buffers were considered positive if 10 or more colonies were counted, and the presence of malodorous vaginal discharges was the clinical sign of the occurred infection.

The efficacy of vaginal tablets prepared as in Example 1 with different rifaximin doses, expressed according to the percent eradication of the infection caused by *Gardnerella* spp. in the rabbit is reported in Table 16.

TABLE 16

| Number of animals | Rifaximin Dose (mg) | Eradication (%) | |
|---|---|---|---|
| | | After 3 days | After 7 days |
| 6 | 0 | 0 | 0 |
| 8 | 1.5 | 88 | 100 |
| 8 | 3 | 63 | 100 |
| 8 | 6 | 88 | 100 |
| 12 | 12.5 | 100 | 100 |

The efficacy of vaginal ovules prepared as in Example 4 with different rifaximin doses at eradicating the persistent infection caused by *Gardnerella* spp. in the rabbit, is expressed as a percentage of eradication and it is reported in Table 17.

TABLE 17

| Number of animals | Rifaximin Dose (mg) | Eradication (%) | |
|---|---|---|---|
| | | After 3 days | After 7 days |
| 6 | 0 | 0 | 0 |
| 8 | 1.5 | 100 | 100 |
| 8 | 3 | 88 | 100 |
| 8 | 6 | 88 | 100 |
| 12 | 12.5 | 100 | 100 |

The analysis of rabbits treated with rifaximin were negative for 7 days after the end of the treatment, whereas the non treated rabbits (control rabbits) remained infected.

After the treatment also all clinical signs disappeared.

Example 10

Determination of Systemic Absorption, Local and Systemic Tolerability with a Pharmacokinetic Study (Clinical Trial Phase I) of Rifaximin Vaginal Tablets A Phase I, on healthy volunteers is carried out to evaluate the possible systemic absorption and local and systemic tolerability of rifaximin vaginal tablets after single administration via the vaginal route was determinate.

A single dose rifaximin vaginal tablets 100 mg, prepared as described in Example 8, was administered to 24 healthy volunteers having an age comprised between 18 and 50 years.

Blood samples were taken from each subject (S) before the administration (time 0) and after the administration, namely after 30 minutes, 1, 1.5, 2, 3, 4, 6, 8, 10, 12, 16 and 24 hours after the administration of the single dose of rifaximin vaginal tablets 100 mg. The samples were analyzed by liquid chromatography equipped with mass spectrometry detector, with a lower limit of quantization (LLOQ) of rifaximin concentration 0.5 ng/ml.

All rifaximin plasma concentrations, at different times, in the analyzed subjects, turned out to be under the analytical detection limit.

Example 11

Determination of Tolerability after Administration of Rifaximin Vaginal Tablets

In Phase I study it has also been evaluated, local and systemic tolerability on 24 healthy volunteers after a single administration of a vaginal tablet containing 100 mg rifaximin.

No subject showed vaginal itching or pain at different times after the administration, thus confirming a good local tolerability. Only a volunteer showed a light vaginal pain, spontaneously ended a few hours later.

For the evaluation of systemic tolerability vital signs such as ECG, biochemical parameters in blood and urine, and adverse events reported by the volunteers were monitored. The absence of detectable systemic concentrations of rifaximin and systemic symptoms indicates a good tolerability of the vaginal tablet containing 100 mg rifaximin.

Example 12

Treatment of Bacterial Vaginosis with Rifaximin Vaginal Tablets

The example describes the clinical trial Phase II carried out on 114 patients affected by bacterial vaginosis, non-pregnant, having an age between 18 and 50 years.

The diagnosis of bacterial vaginosis was based on Amsel criteria, wherein at least three criteria out of four must be positive, and on the Nugent score, wherein a score higher than four indicates the presence of pathogenic vaginal bacteria.

The objectives of the trial were the evaluation of recovery from bacterial vaginosis both according to Amsel criteria (Amsel index <3) and according to Nugent score (Nugent index <4) 7-10 days after the end of the therapy.

The secondary objectives of the trial were the recovery, separately evaluated according to Amsel criteria and to Nugent score, at the first control visit (V3), the continued recovery at the second control visit (V4) and the evaluation of the composition of vaginal microbiota by means of PCR and PCR-DGGE.

In particular, the patients affected by bacterial vaginosis and not affected by contemporaneous viral, protozoan and fungal vaginal infections were assigned to one of the following treatment groups using a centralized randomization procedure and a double-blind experimental design:

Group A: 21 patients receiving a vaginal tablet of rifaximin containing 100 mg rifaximin, prepared according to Example 2, once a day for five days, in the evening;

Group B: 23 patients receiving a vaginal tablet of rifaximin containing 25 mg rifaximin, prepared according to Example 1, once a day for five days, in the evening;

Group C: 19 patients receiving a vaginal tablet of rifaximin containing 100 mg rifaximin, prepared according to Example 2, once a day for two days, in the evening, plus a vaginal tablet of placebo, once a day for the remaining three days, in the evening;

Group D: 22 patients receiving a placebo tablet prepared according to Example 1, wherein the rifaximin amount was replaced by lactose monohydrate, once a day for five days, in the evening.

The study included a screening visit (V1) followed by a randomization visit after seven days (V2), by a first control visit 7-10 days after the end of the therapy (V3) and by a second and last control visit 28-35 days after the end of the therapy (V4). The evaluation of the attainment of the primary objective was carried out during visit V3, and the evaluation of the attainment of the secondary objectives was evaluated during the second and last visit (V4). Table 18 reports the percent recovery from the disease at the visit V3, according to both evaluation criteria, namely the clinical one (Amsel) and the microbiological (Nugent).

TABLE 18

Recovery from the disease at the visit V3 according to both evaluation criteria, the clinical one (Amsel) and the microbiological one (Nugent)

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| Recovered patients (%) | 25.9 | 48.0 | 36.0 | 19.2 |

The recovery evaluated according to Amsel clinical criteria at the visit V3 is reported in Table 19.

TABLE 19

Recovery from the disease at the visit V3 according to the clinical evaluation criteria (Amsel)

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| Recovered patients (%) | 66.7 | 80.0 | 72.0 | 42.3 |

The recovery was evaluated according to Nugent score by using a Gram stained slide and by evaluating the proportion between *Lactobacilli* and other bacteria such as Gram-variable or Gram-negative coccobacilli, Gram-variable curved bacilli.

Table 20 reports the values obtained in the various groups of patients treated according to Nugent criteria.

TABLE 20

Recovery from the disease at the visit V3 according to the microbiological evaluation criteria (Nugent)

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| Recovered patients (%) | 25.9 | 48.0 | 36.0 | 19.2 |

The continued recovery was evaluated at the fourth visit V4. Table 21 reports the percent recovery from the disease at the visit V4.

TABLE 21

Recovery from the disease at the visit V4 according to both evaluation criteria, the clinical one (Amsel) and the microbiological one (Nugent)

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| Recovered patients (%) | 14.8 | 28.0 | 4.0 | 7.7 |

TABLE 22

Recovery from the disease at the visit V4 according to both evaluation criteria, the clinical one (Amsel) and the microbiological one (Nugent) in patients suffering from a first episode or a relapse of bacterial vaginosis

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| Recovery of patients suffering from a first episode of bacterial vaginosis (%) | 14.3 | 41.7 | 25.0 | 21.4 |
| Recovery of patients after relapse of bacterial vaginosis (%) | 38.5 | 53.8 | 46.2 | 16.7 |

The determination of the adverse event was carried out by evaluating both local and systemic effects in patients taking the rifaximin tablets.

The adverse events reported by patients were registered, and the most frequent one was the rifaximin related vulvovaginal itching and burning.

In Table 23 it is reported the percentage of patients belonging to different treatment groups who reported adverse events both systemic and local, vulvovaginal itching and burning related to rifaximin.

TABLE 23

Frequency of adverse events

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| Patients with adverse events (%) | 35.7 | 34.6 | 7.7 | 46.0 |
| Patients with vulvovaginal itching (%) | 25.0 | 19.2 | 3.8 | 19.2 |
| Patients with vulvovaginal burning (%) | 3.6 | 19.2 | 3.8 | 30.8 |

No rifaximin related vulvovaginal candidiasis were showed during treatment in any of the treated groups.

Example 13

Evaluation of Patients Showing a Decrease Greater than or Equal to 3 Points at the Visit at the End of the Treatment (V3) When Compared to the Visit Before the Therapy Patients enrolled in the clinical trial and belonging to treatment groups A, B, C and D, as described in Example 12, showed at the visit before the therapy Nugent score values between 7 and 10.

Table 24 reports the number and percentage of patients who, at the visit at the end of the therapy, showed a decrease of Nugent score higher than or equal to 3 points.

TABLE 24

Decrease ≥3 points of Nugent score at the visit V3

| | Group | | | |
|---|---|---|---|---|
| | A | B | C | D |
| Administered dose | Rifaximin 1 tablet 100 mg × 5 days | Rifaximin 1tablet 25 mg × 5 days | Rifaximin 1 tablet 100 mg × 2 days | Placebo |
| Patients with decreased Nugent score ≥3 points (%) | 52.4 | 65.2 | 36.9 | 18.2 |

Example 14

Evaluation of Patients Showing a Decrease Greater than or Equal to 3 Points at the Visit at the End of the Treatment (V3) in Comparison to the Visit Before the Therapy (V1)

Patients enrolled in the clinical trial and belonging to treatment groups A, B, C and D, as described in Example 12, showed at the visit before the therapy Nugent score values between 7 and 10.

Table 25 reports the number and percentage of patients who, at the visit at the end of the therapy, showed a decrease of Nugent score higher than or equal to 5 points.

TABLE 25

Decrease ≥5 points of Nugent score at the visit V3

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| Patients with decreased Nugent score ≥5 points (%) | 28.6 | 47.8 | 26.3 | 0.1 |

Example 15

Evaluation of Patients Showing a Decrease Higher than or Equal to 8 Points at the Visit at the End of the Treatment (V3) when Compared to the Visit Before the Therapy (V1)

Patients enrolled in the clinical trial and belonging to treatment groups A, B, C and D, as described in Example 12, showed at the visit before the therapy Nugent score values between 7 and 10.

Table 26 reports the number and percentage of patients who, at the visit at the end of the therapy, showed a decrease of Nugent score higher than or equal to 8 points.

TABLE 26

Decrease ≥8 points of Nugent score at the visit V3

| | Group | | | |
|---|---|---|---|---|
| | A | B | C | D |
| Administered dose | Rifaximin 1 tablet 100 mg × 5 days | Rifaximin 1tablet 25 mg × 5 days | Rifaximin 1 tablet 100 mg × 2 days | Placebo |
| Patients with decrease Nugent score ≥8 points (%) | 14.29 | 17.39 | 15.79 | 0 |

Example 16

Determination of Patients not Responding to the Therapy with the Vaginal Tablets Comprising Rifaximin Patients enrolled in the clinical study and belonging to treatment groups A, B, C and D, as described in Example 12, showed at the visit before the therapy Nugent score values comprised between 7 and 10.

Table 27 reports the number and percentage of patients who, at the visit at the end of the therapy, did not respond to the therapy itself, registering a decrease of Nugent score of 0 points, or showed a worsening of the disease, thus registering an increase of the Nugent score.

TABLE 27

Decrease 0 points of Nugent score at the visit V3

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |

TABLE 27-continued

Decrease 0 points of Nugent score at the visit V3

| | Group | | | |
|---|---|---|---|---|
| | A | B | C | D |
| Patients with decreased Nugent score ≤0 points (%) | 9.52 | 17.39 | 36.84 | 68.18 |

Example 17

Determination of the Composition of Vaginal Microbiota with Quantitative Real-Time PCT Technique, at the Visits V1 and V3

During the clinical trial, described in Example 12, samples of vaginal cleansing were collected and the composition of vaginal microbiota was determined by means of the quantitative real-time PCR.

With the real-time PCR the DNA samples are amplified with gender- and/or species-specific primers whose target is the 16S rRNA bacterial gene or the 16S-23 S rRNA region.

In particular, specific probes were used for the *Lactobacillus* gender, for *Gardnerella vaginalis*, for *Atopobium*, for *Prevotella* and for *Veillonella*, since they represent the main bacterial groups suffering from modifications in case of bacterial vaginosis.

Table 28 reports the values of real-time PCR relating to bacterial genders and species quantified in vaginal cleansings of women belonging to the different treatment groups, expressed as total target DNA ng/genomic DNA µg, for microbial species tested for each group at the visit V3 if compared to the visit V1.

TABLE 28

| | | | Target DNA/genomic vaginal DNA (ng/µg) (average ± SD) | | | | |
|---|---|---|---|---|---|---|---|
| Group | Dose | Visit | Lactobacillus | Gardnerella vaginalis | Atopobium | Prevotella | Veillonella |
| A | Rifaximin 1 tablet 100 mg × 5 days | V1[i] | 1.683E+01 ± 1.695E+00 | 3.492E+01 ± 7.994E+00 | 9.307E+01 ± 7.086E+00 | 1.880E+01 ± 3.182E+00 | 4.128E-02 ± 1.341E-02 |
| | | V3[i] | 2.009E+01 ± 2.885E+00 | 2.356E+01 ± 3.386E+00 | 6.146E+01 ± 3.623E+00 | 1.220E+01 ± 1.324E+00 | 7.807E-03 ± 4.069E-03 |
| B | Rifaximin 1 tablet 25 mg × 5 days | V1[ii] | 1.006E+01 ± 6.863E-01 | 1.194E+02 ± 1.393E+01 | 1.082E+02 ± 1.388E+01 | 1.847E+01 ± 1.308E+00 | 3.492E-02 ± 1.118E-02 |
| | | V3[ii] | 3.378E+01 ± 4.434E+00 | 6.626E+01 ± 1.312E+01 | 4.880E+01 ± 1.444E+01 | 3.712E+00 ± 8.556E-01 | 1.761E-02 ± 8.451E-03 |
| C | Rifaximin 1 tablet 100 mg × 2 days | V1[iii] | 1.266E+01 ± 1.378E+00 | 6.674E+01 ± 9.774E+00 | 1.704E+02 ± 2.164E+01 | 1.791E+01 ± 2.802E+00 | 2.214E-01 ± 5.992E-02 |
| | | V3[iii] | 2.536E+01 ± 2.110E+00 | 2.944E+01 ± 6.199E+00 | 5.999E+01 ± 1.260E+01 | 7.248E+00 ± 2.176E+00 | 5.642E-03 ± 2.001E-03 |
| D | Placebo | V1[iv] | 1.488E+01 ± 1.482E+00 | 1.272E+02 ± 1.406E+01 | 1.210E+02 ± 1.943E+01 | 1.729E+01 ± 3.359E+00 | 1.878E-02 ± 3.581E-03 |
| | | V3[iv] | 9.040E+00 ± 1.039E+00 | 6.674E+01 ± 8.032E+00 | 5.671E+01 ± 1.015E+01 | 1.292E+01 ± 2.537E+00 | 4.826E-02 ± 1.600E-02 |

[i] 27 patients;
[ii] 25 patients;
[iii] 25 patients;
[iv] 25 patients

Comparing the values at the visit V1 to the ones at the visit V4, the results show that the amounts of all pathogenic species were reduced, whereas in the same comparison the *Lactobacilli* were increased. In particular, for Group B these differences were all statistically remarkable, with the exception of *Veillonella*.

Example 18

Determination of the Composition of Vaginal Microbiota with Quantitative Real-Time PCR at the Visits V1 and V4 After Treatment with the Rifaximin Vaginal Tablets The composition of vaginal microbiota was determined by means of the quantitative real-time PCR technique of patients maintaining their recovery at the visit V4, 30-40 days after the end of the therapy, and the DNA samples amplified with gender- and/or species-specific primers were evaluated by means of the real-time PCR technique.

In particular, specific probes were used for the *Lactobacillus* gender, for *Gardnerella vaginalis*, for *Atopobium*, for *Prevotella* and for *Veillonella*, since they represent the main bacterial groups suffering from modifications in case of bacterial vaginosis.

Table 29 reports the values of real-time PCR relating to target bacterial genders and species quantified in vaginal rinses of women belonging to the different treatment groups, expressed as total target DNA ng/genomic DNA µg, for microbial species tested for each group at the visit V4 when compared to the values observed at the visit V1 of all treated patients.

TABLE 29

| Group | Dose | Visit | Target DNA/genomic or vaginal DNA (ng/µg)(average ± SD) | | | | |
|---|---|---|---|---|---|---|---|
| | | | Lactobacillus | Gardnerella vaginalis | Atopobium | Prevotella | Veillonella |
| A | Rifaximin 1 tablet 100 mg × 5 days | V1[i] | 1.683E+01 ± 1.695E+00 | 3.492E+01 ± 7.994E+00 | 9.307E+01 ± 7.086E+00 | 1.880E+01 ± 3.182E+00 | 4.128E−02 ± 1.341E−02 |
| | | V4[ii] | 2.130E+01 ± 2.152E+00 | 3.067E+00 ± 2.904E−01 | 5.348E+00 ± 5.819E−01 | 4.296E−02 ± 1.232E−02 | 0.000E+00 ± 0.000E+00 |
| B | Rifaximin 1 tablet 25 mg × 5 days | V1[iii] | 1.006E+01 ± 6.863E−01 | 1.194E+02 ± 1.393E+01 | 1.082E+02 ± 1.388E+01 | 1.847E+01 ± 1.308E+00 | 3.492E−02 ± 1.118E−02 |
| | | V4[iv] | 3.957E+01 ± 9.400E+00 | 1.757E+01 ± 2.908E+00 | 2.825E+01 ± 2.719E+00 | 2.345E+00 ± 2.348E−01 | 0.000E+00 ± 0.000E+00 |
| C | Rifaximin 1 tablet 100 mg × 2 days | V1[v] | 1.266E+01 ± 1.378E+00 | 6.674E+01 ± 9.774E+00 | 1.704E+02 ± 2.164E+01 | 1.791E+01 ± 2.802E+00 | 2.214E−1 ± 5.992E−02 |
| | | V4[vi] | 8.959E+00 ± 1.725E+00 | 7.509E+01 ± 1.295E+01 | 1.399E+02 ± 1.708E+01 | 5.400E+01 ± 1.003E+01 | 2.748E−01 ± 1.020E−01 |
| D | Placebo | V1[vii] | 1.488E+01 ± 1.482E+00 | 1.272E+02 ± 1.406E+01 | 1.210E+02 ± 1.943E+01 | 1.729E+01 ± 3.359E+00 | 1.878E−02 ± 3.581E−03 |
| | | V4[viii] | 1.408E+01 ± 9.778E−01 | 6.095E+01 ± 4.117E+00 | 2.537E+01 ± 1.323E+00 | 1.444E−01 ± 3.709E−02 | 0.000E+00 ± 0.000E+00 |

[i] 27 patients;
[ii] 6 patients;
[iii] 25 patients;
[iv] 12 patients;
[v] 25 patients;
[vi] 9 patients;
[vii] 9 patients;
[viii] 4 patients.

TABLE 30

Percent of patients with clusterizing profiles

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| V1 vs. V3 (%) | 37 | 24 | 28 | 56 |
| V1 vs. V3 vs. V4 (%) | 0 | 0 | 11 | 50 |

The results reported in Table 30 show that there is high variability in the bacterial population identified at V1, V3 and V4 in patients treated with rifaximin preparations, thus showing that the vaginal microbiota was significantly modified by the pharmacological action of rifaximin at the concentrations released by the administered preparations.

In particular, it turns out that the preparation administered to Group B patients is most effective at the visit V3.

The effect of rifaximin preparations was further confirmed after the visit V4, wherein, in particular in Groups A and B, the bacterial population is radically modified.

In order to evaluate the pharmacological action of the examined rifaximin preparations, different treatment groups were compared through the so called Similarity Indexes (SI). The analysis consists in evaluating the similarity of electrophoretic profiles calculated on the basis of the Pearson correlation coefficient. In the examined case, SI indicates the percent similarity between two or more DGGE profiles belonging to the same woman at the different visits.

Example 19

Determination of the Composition of Vaginal Microbiota with the PCR-DGGE after Treatment with the Rifaximin Preparations During the clinical trial samples of vaginal rinses were taken, and the composition of vaginal microbiota was determined by means of the PCR-DGGE technique, allowing the identification of various bacterial DNA through an electrophoretic process and a DNA amplification with universal primers for the bacterial 16S rRNA region. The result of this technique was a sequence of visible bands, called clusters, wherein each of them is representative for the DNA of bacterial species present in the considered sample.

The analysis of clusters of DGGE profiles of samples, carried out by using the FPQuest software (Bio-Rad) gives the information relating to the similarity of two samples. In the specific case wherein the recovery is intended as reduction of pathogenic species, it is positive that the sample of a patient after treatment is quite different from the sample of the same patient before treatment.

The analysis was carried out with vaginal samples at the visits V1, V3 and V4 for the four groups A, B, C and D of treated patients. Table 30 reports the percent of patients with "clusterizing" profiles.

TABLE 31

Similarity Index

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| V1-V3 | 61.6 | 48.4 | 54.0 | 75.4 |
| V1-V4 | 52.1 | 40.0 | 47.1 | 57.6 |
| V3-V4 | 66.8 | 62.1 | 42.8 | 58.7 |
| V1-V3-V4 | 50.8 | 36.4 | 37.6 | 56.7 |

The results of Table 31 indicate that in the comparison case V1-V3 the similarity index of the groups treated with the rifaximin preparations is significantly different from the one of the placebo group.

Another adopted criterion of evaluation of the samples is the so called Richness Index (RI). This criterion, based on the bands of each DGGE profile, gives the measure of the complexity of the bacterial population, which is a sign of disease for the occurrence of new pathogenic species. Table 32 reports the RI average values, measured at the visits V1 and V3.

TABLE 32

Richness Index

| | Group | | | |
|---|---|---|---|---|
| | A | B | C | D |
| Administered dose | Rifaximin 1 tablet 100 mg × 5 days | Rifaximin 1 tablet 25 mg × 5 days | Rifaximin 1 tablet 100 mg × 2 days | Placebo |
| V1 | 13.5 | 14.0 | 15.4 | 13.3 |
| V3 | 10.9 | 10.7 | 12.2 | 13.9 |

The results of Table 32 show that the profiles of vaginal microbiota become less complex in the groups treated with the rifaximin preparations when they are compared to the placebo treated group.

What is claimed is:

1. A pharmaceutical composition comprising:
   (a) rifaximin granules comprising an amorphous form or a crystalline form of rifaximin, in an amount less than 500 mg and one or more of an intragranular excipient; and
   (b) one or more of an extragranular excipient including at least one disintegrant;
   wherein said pharmaceutical composition has selective bactericidal activity against vaginal pathogenic bacteria; and
   wherein the disintegrant is crospovidone or a mixture of crospovidone and calcium silicate.

2. A pharmaceutical composition comprising:
   (a) rifaximin granules comprising an amorphous form or a crystalline form of rifaximin, in an amount less than 500 mg and one or more of an intragranular excipient; and
   (b) one or more of an extragranular excipient including at least one disintegrant;
   wherein said pharmaceutical composition has selective bactericidal activity against vaginal pathogenic bacteria; and
   wherein the intragranular excipient comprises a binder selected from the group consisting of pregelatinized starch, arabic gum, maltodextrine, copovidone, saccharose and mixtures thereof.

3. The pharmaceutical composition according to claim 2, wherein the binder is copovidone.

4. A pharmaceutical composition comprising:
   (a) rifaximin granules comprising an amorphous form or a crystalline form of rifaximin, in an amount less than 500 mg and one or more of an intragranular excipient; and
   (b) one or more of an extragranular excipient including at least one disintegrant;
   wherein said pharmaceutical composition has selective bactericidal activity against vaginal pathogenic bacteria; and
   wherein the composition further comprises bioadhesive agents, buffering agents, or mixtures thereof.

5. A pharmaceutical composition comprising:
   (a) rifaximin granules comprising an amorphous form or a crystalline form of rifaximin, in an amount less than 500 mg and one or more of an intragranular excipient; and
   (b) one or more of an extragranular excipient including at least one disintegrant;
   wherein said pharmaceutical composition has selective bactericidal activity against vaginal pathogenic bacteria; and
   wherein the rifaximin is in a polymorphic form.

6. A controlled release dosage form of a pharmaceutical composition, wherein the pharmaceutical composition comprises
   (a) rifaximin granules comprising an amorphous form or a crystalline form of rifaximin in an amount less than 500 mg and one or more of an intragranular excipient; and
   (b) one or more of an extragranular excipient including at least one disintegrant; wherein the pharmaceutical composition has selective bactericidal activity against at least one of Gardnerella vaginalis, Mycoplasma hominis, Bacteroides Atopobium vaginale, Peptostreptococcus, Mobiluncus, Prevotella and Veillonella;
   wherein the disintegrant is crospovidone or a mixture of crospovidone and calcium silicate.

7. A pharmaceutical composition comprising:
   (a) rifaximin granules comprising an amorphous form or a crystalline form of rifaximin, in an amount less than 500 mg and one or more of an intragranular excipient; and
   (b) one or more of an extragranular excipient including at least one disintegrant;
   wherein said pharmaceutical composition has selective bactericidal activity against vaginal pathogenic bacteria; and
   further comprising buffering agents, antiseptic agents, or antibiotic agents or mixtures thereof.

8. A pharmaceutical composition formulated for vaginal administration, the pharmaceutical composition comprising:
   an amorphous form or a crystalline form of rifaximin in an amount less than 500 mg and one or more of an intragranular excipient in granules wherein the intragranular excipients consist of a binder, diluents, lubricants or mixtures thereof; and
   one or more of an extragranular excipient including at least one disintegrant;
   wherein said pharmaceutical composition has selective bactericidal activity against vaginal pathogenic bacteria; and
   further comprising a bioadhesive agent.

* * * * *